(12) United States Patent
Moody et al.

(10) Patent No.: US 11,090,457 B2
(45) Date of Patent: Aug. 17, 2021

(54) MEDICAL TUBES AND CONNECTORS FOR GASES DELIVERY SYSTEMS

(71) Applicant: Fisher & Paykel Healthcare Limited, Auckland (NZ)

(72) Inventors: Paul Joseph Moody, Auckland (NZ); Sven Andreas Munkelt, Hermsdorf (DE); Katie Fyfe, Auckland (NZ); Telge Nishan Chaturanga Peiris, Auckland (NZ); Kevin Blake Powell, Auckland (NZ); Bhavna Prentice, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 275 days.

(21) Appl. No.: 15/324,235

(22) PCT Filed: Jul. 7, 2015

(86) PCT No.: PCT/NZ2015/050083
§ 371 (c)(1),
(2) Date: Jan. 5, 2017

(87) PCT Pub. No.: WO2016/007019
PCT Pub. Date: Jan. 14, 2016

(65) Prior Publication Data
US 2017/0197055 A1    Jul. 13, 2017

Related U.S. Application Data

(60) Provisional application No. 62/021,591, filed on Jul. 7, 2014, provisional application No. 62/054,559, filed
(Continued)

(51) Int. Cl.
*A61M 16/08* (2006.01)
*A61M 16/16* (2006.01)
(Continued)

(52) U.S. Cl.
CPC ...... *A61M 16/0875* (2013.01); *A61M 13/003* (2013.01); *A61M 16/0816* (2013.01);
(Continued)

(58) Field of Classification Search
CPC ............ A61M 16/0875; A61M 13/003; A61M 16/1095; A61M 16/0816; A61M 16/16;
(Continued)

(56) References Cited

U.S. PATENT DOCUMENTS 3,163,707 A * 12/1964 Darling ...................... A47L 9/24
174/47
4,686,354 A * 8/1987 Makin ............... A61M 16/1075
128/204.17
(Continued)

FOREIGN PATENT DOCUMENTS

EP       2329858       6/2011
WO    WO 2007/104045    9/2007
(Continued)

OTHER PUBLICATIONS

Definition of "Edge", Macmillandictionary, captured on Oct. 23, 2020.*
(Continued)

*Primary Examiner* — Tu A Vo
(74) *Attorney, Agent, or Firm* — Knobbe Martens Olson & Bear LLP

(57) ABSTRACT

A medical circuit including a medical tube and a connector transports gases to and/or from a patient via a patient interface. The connector has a plurality of rigid components at least partially surrounded by an overmold. The medical tube has a first elongate member and a second elongate member. The first elongate member is substantially hollow. A vent can be coupled to the first elongate member such that it maintains gaseous communication with the lumen. The
(Continued)

vent may provide a pathway between the lumen and the atmosphere, such that gases may move into and/or out of the lumen during cleaning. The vent may also provide a barrier to liquid and/or substance ingress into the first elongate member during cleaning of the medical circuit. The medical circuit can be reusable.

21 Claims, 15 Drawing Sheets

Related U.S. Application Data on Sep. 24, 2014, provisional application No. 62/084,259, filed on Nov. 25, 2014, provisional application No. 62/132,780, filed on Mar. 13, 2015.

(51) Int. Cl.
A61M 16/10 (2006.01)
A61M 13/00 (2006.01)
A61M 16/00 (2006.01)

(52) U.S. Cl.
CPC .... *A61M 16/0841* (2014.02); *A61M 16/1095* (2014.02); *A61M 16/16* (2013.01); *A61M 16/0069* (2014.02); *A61M 16/109* (2014.02); *A61M 2205/33* (2013.01); *A61M 2205/3368* (2013.01)

(58) Field of Classification Search
CPC .......... A61M 16/0841; A61M 2205/33; A61M 16/109; A61M 16/0069; A61M 2205/3368; A61M 16/142; A61M 16/04; A61M 16/0402; A61M 16/0461; A61M 16/0465; A61M 16/08; A61M 1/00; A61M 39/00; A61M 16/00; A61M 16/1045

See application file for complete search history.

(56) References Cited

U.S. PATENT DOCUMENTS

| | | | | |
|---|---|---|---|---|
| 5,357,948 | A * | 10/1994 | Eilentropp | A61M 16/08 128/203.26 |
| 6,078,730 | A * | 6/2000 | Huddart | A61M 16/08 219/536 |
| 7,140,366 | B2 * | 11/2006 | Smith | A61M 16/08 128/203.16 |
| 7,469,719 | B2 * | 12/2008 | Gray | A61M 16/08 128/203.26 |
| 7,857,645 | B2 * | 12/2010 | Dude | F16L 53/38 439/191 |
| 10,213,571 | B2 | 2/2019 | Coleman et al. | |
| 2008/0092973 | A1 * | 4/2008 | Lai | F16L 11/11 138/118 |
| 2008/0105257 | A1 * | 5/2008 | Klasek | A61M 16/0633 128/203.27 |
| 2010/0083965 | A1 * | 4/2010 | Virr | A61M 16/0875 128/203.26 |
| 2010/0116272 | A1 * | 5/2010 | Row | A61M 16/0816 128/204.17 |
| 2011/0126838 | A1 | 6/2011 | Alberici et al. | |
| 2013/0112201 | A1 * | 5/2013 | Graham | A61M 16/0875 128/203.27 |
| 2014/0053939 | A1 * | 2/2014 | Kaye | A61M 39/12 138/109 |
| 2014/0158130 | A1 | 6/2014 | Coleman et al. | |
| 2014/0236083 | A1 * | 8/2014 | Sims | A61M 16/0816 604/114 |
| 2015/0306332 | A1 * | 10/2015 | Bafile | A61M 16/0666 128/202.27 |
| 2019/0070382 | A1 | 3/2019 | Coleman et al. | |

FOREIGN PATENT DOCUMENTS

| | | | |
|---|---|---|---|
| WO | WO 2008/055308 | 5/2008 | |
| WO | WO 2009/109005 | 9/2009 | |
| WO | WO 2012154064 A2 * | 11/2012 | ........ A61M 16/0875 |
| WO | WO 2012/164407 | 12/2012 | |
| WO | WO 2015/142192 | 9/2015 | |

OTHER PUBLICATIONS

International Search Report dated Nov. 23, 2015 for PCT Application No. PCT/NZ2015/050083.

Extended European Search Report dated Feb. 12, 2018 for European Application No. 15818962.1.

Chinese Office Action dated Nov. 29, 2018 for Chinese Application No. 201580047283.8.

* cited by examiner

MEDICAL TUBES AND CONNECTORS FOR GASES DELIVERY SYSTEMS

INCORPORATION BY REFERENCE

This application is a national phase of International Application No. PCT/NZ2015/050083, filed Jul. 7, 2015, and published on Jan. 14, 2016 as International Publication No. WO 2016/007019, which claims priority to U.S. Provisional Application No. 62/021,591, filed Jul. 7, 2014, U.S. Provisional Application No. 62/054,559, filed Sep. 24, 2014, U.S. Provisional Application No. 62/084,259, filed Nov. 25, 2014, and U.S. Provisional Application No. 62/132,780, filed Mar. 13, 2015, the entire contents of each of which are incorporated herein by reference.

BACKGROUND

Technical Field

The present disclosure relates generally to medical tubes and connectors to deliver gases to patients and more particularly to reusable medical tubes and connectors for gases delivery systems, such as respiratory assistance and insufflation systems.

Description of the Related Art

A gases delivery system delivers gases to a patient. Gases delivery systems include respiratory assistance systems and insufflation systems. The gases may be heated and/or humidified prior to delivery to the patient. The gases are conveyed from a humidifier or other gases source via a medical circuit to a patient interface. A medical circuit may be formed from a medical tube and one or more connectors and may be disposable or reusable. To prevent condensate formation within the medical tube, the medical tube may be insulated and/or heated using a heater wire. A connector for a gases delivery system may comprise a rigid body that can be integrally coupled to a medical tube.

SUMMARY

Medical tubes, connectors, and methods of manufacturing medical tubes and connectors are disclosed herein in various embodiments.

According to at least one aspect of the present disclosure, a medical circuit for a gases delivery system can have one, some, or all of the following features, as well as other features described herein. The medical circuit comprises a medical tube. The medical tube comprises a first elongate member. The first elongate member comprises a lumen. The medical circuit comprises a vent coupled to the first elongate member such that it maintains gaseous communication with the lumen of the first elongate member. The vent allows gaseous communication between the lumen of the first elongate member and the atmosphere. The vent substantially prevents ingress of liquid into the lumen of the first elongate member.

The vent can comprise a material with a low surface tension. The vent can be inserted directly into the lumen of the first elongate member. The vent can be coupled to the first elongate member via a housing. The housing can be inserted into the lumen of the first elongate member. The housing can couple the vent to the first elongate member via an inner conduit. The housing can be coupled with a connector via overmolding. The medical tube can comprise a second elongate member. The second elongate member can comprise heater wires. The second elongate member can comprise sensing wires. The second elongate member can comprise a combination of heater wires and sensing wires. The housing can comprise an electrical connection between the heater wires and/or the sensing wires and the connector. The housing can comprise a gases pathway from the vent to the atmosphere. The housing can comprise a plug and a receiving portion. The housing can comprise a piercing member. The vent can be made from polytetrafluoroethylene. The vent can be a solid component. The vent can be a film.

According to at least one aspect of the present disclosure, a medical circuit for a gases delivery system can have one, some, or all of the following features, as well as other features described herein. The medical circuit comprises a medical tube. The medical tube comprises a first elongate member. The medical tube comprises a second elongate member. The medical circuit comprises a connector configured to connect the medical tube to a gases delivery system component. The connector comprises a plurality of rigid components. One or more of the plurality of rigid components forms at least part of a preassembled structure. The preassembled structure is at least partially surrounded by an overmold.

The plurality of rigid components can comprise a rigid cuff, a power adaptor port, and/or a carrier part. The power adaptor port can comprise an internal surface comprising an undercut formed from the overmold. The carrier part can comprise a probe port configured to receive a sensing probe. The probe port can comprise an internal surface comprising an undercut formed from the overmold. The overmold can extend axially beyond the preassembled structure to form a lip. The overmold can comprise a recessed portion that forms a gripping area. The plurality of rigid components can protrude through the overmold to at least partially define the gripping area. The rigid cuff can be configured to form a connection between the medical tube and a gases delivery system component.

According to at least one aspect of the present disclosure, a gases delivery system to deliver gases to a patient can have one, some, or all of the following features, as well as other features described herein. The gases delivery system comprises a gases source. The gases delivery system comprises a humidifier. The humidifier is configured to receive gases provided by the gases source and to heat and/or humidify the gases. The gases delivery system comprises a medical circuit configured to deliver heated and/or humidified gases provided by the humidifier to the patient via a patient interface. The medical circuit comprises a medical tube. The medical tube comprises a first elongate member. The medical tube comprises a second elongate member. The medical circuit comprises a connector. The connector comprises a plurality of rigid components at least partially surrounded by an overmold. The medical circuit is reusable.

According to at least one aspect of the present disclosure, a reusable connector for a gases delivery system can have one, some, or all of the following features, as well as other features described herein. The reusable connector comprises a plurality of rigid components. The reusable connector comprises an overmold. The overmold comprises a recessed portion that forms a gripping region. The plurality of rigid components is at least partially surrounded by the overmold. The plurality of rigid components at least partially defines the gripping region.

The plurality of rigid components can comprise at least one of a rigid cuff, a power adaptor port, and a carrier part. The carrier part can comprise a probe port configured to receive a sensing probe. The overmold can form an undercut on an internal surface of the power adaptor port and/or the probe port.

According to at least one aspect of the present disclosure, a medical circuit for a gases delivery system can have one, some, or all of the following features, as well as other features described herein. The medical circuit comprises a medical tube. The medical tube comprises a first elongate member. The medical tube comprises a second elongate member. The first elongate member comprises a lumen. The medical circuit comprises a connector configured to connect the medical tube to a gases delivery system component. The connector comprises a plurality of rigid components, some of which form at least part of a preassembled structure. The plurality of rigid components comprise a power adaptor port comprising a vent configured to be in gaseous communication with the lumen of the first elongate member via a gases pathway. The vent allows gases to move between the lumen of the first elongate member and the atmosphere. The vent substantially prevents ingress of liquid into the lumen of the first elongate member.

At least part of the preassembled structure can be at least partially surrounded by an overmold. The connector can comprise an edge adjacent the medical tube. A portion of the edge can follow a helical orientation of the first elongate member. The edge can comprise an offset portion. The offset portion can allow the portion of the edge to follow the helical orientation of the first elongate member. The vent can comprise a membrane. The power adaptor port can comprise an inner conduit inserted into the first elongate member and a vent path between the vent and the inner conduit. The medical tube can comprise a compressed or flattened extension portion extending in the connector past a point where the vent communicates with the lumen of the first elongate member.

For purposes of summarizing the disclosed systems and apparatus, certain aspects, advantages and novel features of the disclosed systems and apparatus have been described herein. It is to be understood that not necessarily all such advantages may be achieved in accordance with any particular embodiment of the disclosed systems and apparatus. Thus, the disclosed systems and apparatus may be embodied or carried out in a manner that achieves or optimizes one advantage or group of advantages as taught herein without necessarily achieving other advantages as may be taught or suggested herein.

BRIEF DESCRIPTION OF THE DRAWINGS

These and other features, aspects, and advantages will be described with respect to the following figures, which are intended to illustrate and not to limit the disclosed embodiments.

DETAILED DESCRIPTION

Terminology

Figure 1:
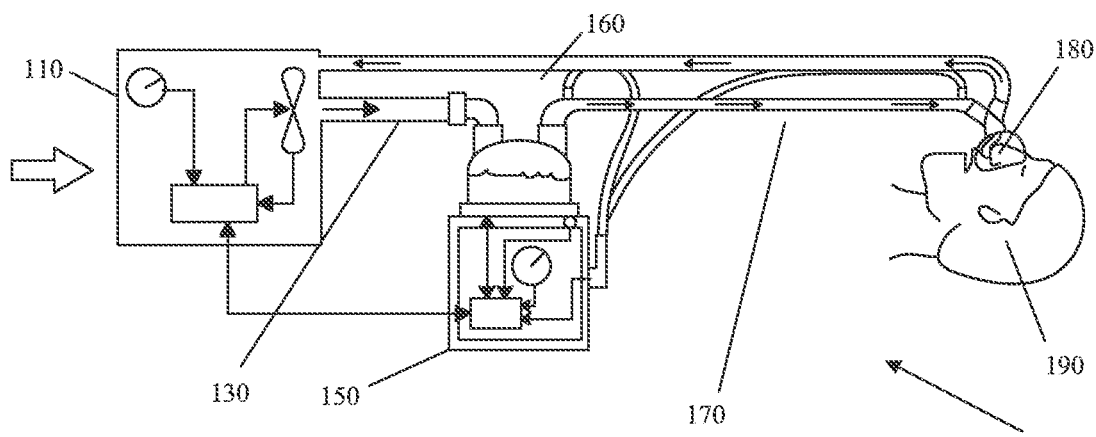
FIG. 1 shows a schematic of a gases delivery system.

A gases delivery system as herein described may refer to a respiratory system or a surgical system such as, but not limited to, a laparoscopic insufflation system.

A vent as herein described may refer to a filter, or medium that has properties that contribute to permeability to gases, and impermeability to another substance or substances, such as a liquid.

Gases as herein described may refer to air, oxygen, carbon dioxide, or any combination of two or more of these.

A substance or substances as herein described may refer to a liquid such as water, detergent, or cleaning chemicals.

A medical tube or circuit as herein described may refer to a tube, conduit, or hose that may transport gases to and/or from a patient via a patient interface. In some embodiments, the medical tube or circuit may transport respiratory or insufflation gases to and/or from a patient.

A patient interface as herein described may refer to a face mask, endotracheal tube, nasal cannula, nasal mask, oral mask, tracheal mask, laparoscopic cannula, or diffuser.

A cycle as herein described may refer to a cleaning cycle. Thus, cleaning a medical tube using conventional cleaning approaches such as autoclaving, soaking, or pasteurizing, either prior to or after use may be termed a cycle.

A reusable medical tube or reusable circuit as herein described may refer to a medical tube or circuit that can undergo multiple cleaning cycles. The medical tube or circuit can thus be reused by the same patient, or by different patients.

A user as herein described may refer to an individual or healthcare provider that prepares the medical tube for the patient. It is to be understood that a user may perform other actions with regards to use of a medical tube that are included in the scope of the present disclosure.

A plurality of heater wires and/or sensing wires as herein described may refer to no heater wires and/or sensing wires, at least one heater wire and/or sensing wires, or multiple heater wires and/or sensing wires. The heater wire may take the form of a heating element or heating filament.

A respiratory assistance system as herein described may refer to a system that delivers respiratory gases, such as oxygen, carbon dioxide, and/or air, or any combination of these, to and/or from a patient.

A gases supply as herein described may refer to an apparatus that supplies gases to a gases delivery system such that the gases may be delivered to a patient. The gases supply may, for example, take the form of a ventilator or blower.

A patient interface as herein described may refer to, but is not limited to, a mask, oral mask, nasal mask, nasal cannula, nasal pillows, endotracheal tube, trache, or tracheal mask.

A gases delivery system component as herein described may refer to, but is not limited to, a humidification apparatus, a humidification chamber, a patient interface, a water trap, a gases supply, a wye-piece, a medical tube, a connector for any these, or any other component or accessory used in a gases delivery system.

Gases Delivery Systems

FIG. 1 shows a schematic of a typical gases delivery system 100, wherein a gases supply 110 supplies gases to a humidification apparatus 150, which supplies heated and humidified gases to a patient 190 via a medical circuit, for example an inspiratory circuit 170, and a patient interface 180. The gases supply 110 and the humidification apparatus 150 may be integrated into a shared housing or may comprise separate housings. In some embodiments, another medical circuit, such as a supply circuit 130, may be used to transport gases from the gases supply 110 to the humidification apparatus 150. In some embodiments, exhaled gases may be transported to the gases supply 110 or elsewhere via another medical circuit, such as an expiratory circuit 160. It is to be understood that some gases delivery systems may not comprise the expiratory circuit 160 and that other variations from the gases delivery system shown may exist.

Medical Circuit

Medical circuits used in hospital settings, such as the expiratory circuit 160, the supply circuit 130, and the inspiratory circuit 170, are often disposable, meant for single patient use and/or a pre-defined maximum duration of use, and thus are disposed of following treatment. Reusable medical circuits have been developed that have a longer lifespan and are able to be cleaned such that they can be reused. Robustness is a key feature of reusable medical circuits, which must undergo many cycles of high level disinfection or sterilisation in between patient uses. As a result, many reusable medical circuits are heavy and cumbersome in use, which may result in patient discomfort.

A heated reusable medical circuit may comprise a heater wire located in the lumen of the medical circuit. The heater wire may need to be removed prior to cleaning. Following cleaning, the heater wire must then be reinserted into the medical circuit and electrically connected to a connector before the medical circuit can be used for the next patient. This process can be complicated and time consuming.

Medical Tube

Figure 2:
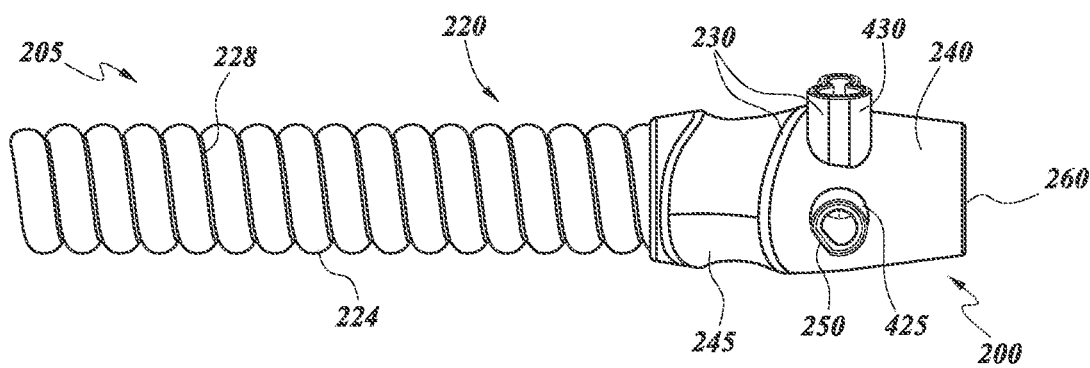
FIG. 2 shows a perspective view of a medical circuit according to an embodiment of the present disclosure.

An example medical circuit 205 is shown in FIG. 2. The medical circuit 205 comprises a medical tube 220 that comprises a first elongate member 224 and a second elongate member 228. The medical tube 220 is described in International Patent Publication No. WO 2014/088430, published Jun. 12, 2014, corresponding to International Patent Application No. PCT/NZ2013/000222, filed Dec. 4, 2013, and entitled MEDICAL TUBES AND METHODS OF MANUFACTURE, which is incorporated herein by reference in its entirety.

Figure 3:
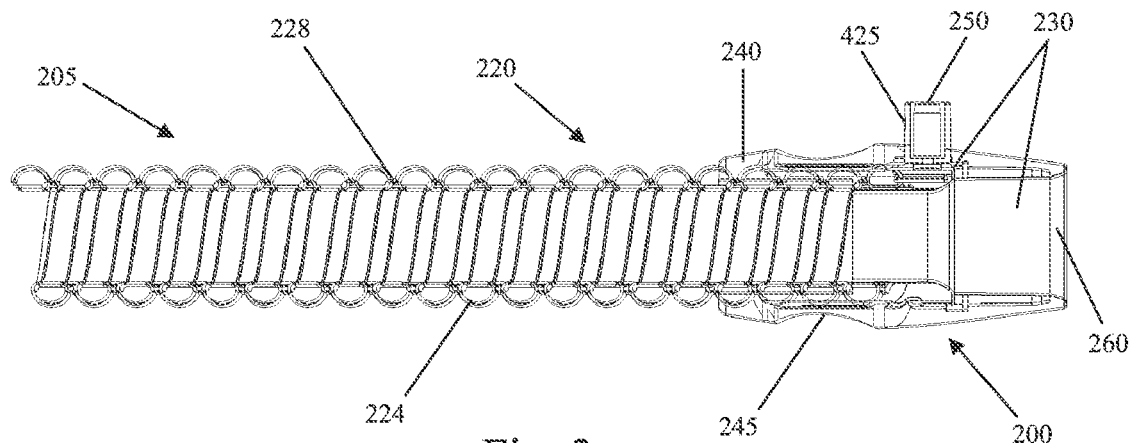
FIG. 3 shows an axial cross-section of the medical circuit according to the embodiment of FIG. 2.

As shown in FIG. 3, the first elongate member 224 is hollow, which enables the medical tube 220 to be lightweight. The first elongate member 224 provides thermal insulation, improved humidity performance, and increased flexibility to the medical tube 220. The first elongate member 224 may be at least partially transparent to enable a user to inspect the lumen of the medical tube 220 for blockage or contaminants, or to confirm the presence of moisture. The medical tube 220 is preferably thermally insulating, and as such prevents or reduces heat loss from the gases transported through the lumen of the medical tube 220 to the atmosphere. The first elongate member 224 can be filled with a gas, for example air, to increase insulating performance.

The second elongate member 228 of FIGS. 2 and 3 acts as structural support for the first elongate member 224. The second elongate member 228 can comprise at least one heater wire or sensing wire (not shown), or a combination of heater and sensing wires. Thus, a heater wire, a sensing wire, or a combination of heater and sensing wires can be integrated into the wall of the medical tube 220. This reduces the steps required to prepare the medical tube 220, and thus the medical circuit 205, for cleaning and for use on a patient. The medical tube 220 is a spirally wound structure comprising a flexible, hollow body and an integral support. This provides crush resistance, while leaving the medical tube 220 flexible enough to permit short-radius bends without kinking, occluding, or collapsing. This structure can also provide a smooth internal wall for the medical tube 220, which helps keep the medical tube 220 free from deposits and improves gas flow.

The medical tube 220 may be constructed of materials having properties that enable the medical tube 220 to withstand the rigorous cleaning approaches of autoclaving, pasteurization, high level disinfection, thermal sterilisation, or soaking in chemicals. The materials for the medical tube 220 can be chosen to make the medical tube 220 easier to manufacture, to make the medical tube 220 lighter weight and less cumbersome than other medical tubes, and to form a bond between the medical tube 220 and a connector that can limit or eliminate areas where dirt or potentially harmful substances may become trapped and that can withstand repeated connection and disconnection of the medical circuit 205 to and from a gases delivery system component.

Connector

In gases delivery systems, connectors are often single use or disposable connectors. In some cases, connectors may be made to be cleaned using washer-disinfector machines, pasteurization, or by soaking and/or autoclaving between patients or between uses, such that a circuit comprising such a connector can be classed as a reusable circuit. Reusable circuits may have a defined duration of use and/or may be designed for a specified number of cleaning or disinfection cycles. Such circuits may be desirable for long term solutions.

A reusable connector may comprise a rigid body with appropriate ports for power adaptors and/or external probes. A connector may have a limited life span following the rigorous cleaning processes it undergoes. In some cases, a connector may have a soft body and a soft taper used to form a connection with a gases delivery system component. In some cases, a connector may have a rigid part suspended within a soft body to provide structural integrity to the body. A medical tube may have a heating component to heat the gases within the tube such that less condensate is produced when using a humidified system. The heating component may be within the lumen of the tube, embedded into the wall of the tube, or outside of the tube. The heating component may need to interact with the connector to form or terminate an electrical connection.

It is recognised that some disadvantages may exist in other connectors. For example, connectors with a soft body and a soft connection cuff, which may in some cases comprise a taper, may have highly variable connection, disconnection, and retention forces, which reduce substantially if the connector is wet. The forces for connection and/or disconnection may be elevated when the connection cuff is dry so that sufficient disconnection and/or retention forces are still achieved when the taper is wet. Thus, the connection or disconnection may require high user force input and may be difficult to use when the connector is not wet.

A heated reusable circuit may have a heating component, such as a heating wire located within the lumen of the circuit. This may need to be removed manually to prepare the circuit for cleaning and may be reinserted into the circuit following the cleaning procedure in preparation for the next use. Such a process may be time consuming, complex, and demanding, thus reducing the overall usability of the circuit.

A rigid connector body may include a plurality of rigid components to interact with a power adaptor and/or probes. Variation of the power adaptors and/or probes may make coupling and/or sealing between these and the plurality of rigid components more difficult.

The materials used for a reusable circuit may not be autoclavable and, thus, may become damaged or may degrade during cleaning procedures. As a result, these cleaning procedures may be limited to only lower temperature procedures. In some cases, the medical tube and the connector may separate in use, which may cause the circuit to be discarded. Some reusable circuits have a limited life span and, thus, may have to be replaced more frequently than desired.

As generally shown in FIG. 2, the circuit 205 comprises a connector 200 that at least partially overcomes or ameliorates at least one disadvantage of other connectors. The connector 200 is adapted to be coupled with the medical tube 220 that comprises the first elongate member 224 and the second elongate member 228. As discussed, the first elongate member 224 may be a hollow structure that provides insulation and flexibility to the medical tube 220, whereas the second elongate member 228 may provide structural support to the medical tube 220 and, in some embodiments, may comprise a heating and/or sensing component. The heating and/or sensing component may be embedded into the wall of the medical tube 220, which may improve the usability aspects of the medical tube 220 while enabling the circuit 205 to be heated.

As discussed in greater detail below, the connector 200 may comprise a plurality of rigid components that can be preassembled before the application of an overmold. As a result, the connector 200 may form a connection between the medical tube 220 and a gases delivery system component via a rigid taper while maintaining a soft connector body. The rigid taper may maintain a lower and more consistent connection, disconnection, or retention force regardless of the connector 200 being wet or dry. The rigid taper may also reduce the impact of side loading on the connection, which may cause disconnection between the medical tube 220 and a gases delivery system component. The soft overmold may also provide a soft surface and, in some embodiments, a flexible protrusion or undercut that may form a sealing ring on the inside of power adaptor ports and/or probe ports. This may improve the seal and coupling between the ports and a power adaptor and/or external probes. The soft surface and sealing ring may compensate for any variation that may occur.

Materials may be used that allow the circuit 205 to be autoclaved. Also, the medical tube 220 and the connector 200 may be made from materials with the same or similar thermal properties, for example the same melting point, which may reduce or eliminate the likelihood of damage to the circuit 205 occurring during manufacturing and cleaning. The circuit 205 may be able to survive at least 50 cleaning cycles with minimal damage, reduction in structural integrity, or alteration to its appearance.

The connector 200 is shown in FIGS. 2 and 3 connected to the medical tube 220. The connector 200 may be permanently attached at either end of the medical tube 220 and may form a connection with a gases delivery system component. In some embodiments, the medical tube 220 and the connector 200 are reusable. The medical tube 220 comprises the first elongate member 224 and the second elongate member 228. The first elongate member 224 may be hollow, which provides an insulating and flexible component to the medical tube 220. The second elongate member 228 may be a more rigid component that provides structural strength to the medical tube 220. In some embodiments, the second elongate member 228 may comprise a heating component and, in some embodiments, a sensing component, such that heating and/or sensing can be embedded into the wall of the medical tube 220. The heating component may be in the form of a plurality of heater wires, for example, two heater wires. The plurality of heater wires may be integrated or embedded into the wall of the medical tube 220.

The first elongate member 224 and the second elongate member 228 cooperate to reduce the condensate formation and to maintain the humidity of the gases as they are transported within the medical tube 220. The connector 200 may provide an electrical interface between an embedded heating component of the medical tube 220 and a gases delivery system component. This electrical connection may be in the form of, for example, an external lead or an integral electrical connector. In some embodiments, the electrical connection may occur between the connector 200 and the electrical source when the connector 200 is connected with a gases delivery system component. An embedded heating component may substantially improve the usability of the circuit 205 when compared with other reusable circuits because the user may not need to disassemble and/or pre-assemble the heating component with regards to the tube in preparation for cleaning and/or future use.

The connector 200 may comprise a plurality of rigid components 230 that provide a structural component as well as a rigid taper for the connection of the connector 200 to a gases delivery system component. The plurality of rigid components 230 may be formed from a rigid material, such as, for example, polypropylene. An overmold 240 coats the plurality of rigid components 230 and provides a soft outer surface for the connector 200. Materials used for the overmold 240 may be, but are not limited to, thermoplastic elastomers.

In some embodiments, a region where the plurality of rigid components 230 protrude through the overmold 240 may at least partially define a gripping region 245. The overmold 240 may, in some embodiments, comprise a recessed and/or contoured portion to accentuate the gripping region 245. An embodiment of the gripping region 245 wherein the plurality of rigid components 230 do not protrude through the overmold 240, or an embodiment which does not comprise a recessed and/or contoured overmolded portion, or any combination of the above, also falls within the scope of the present disclosure. The gripping region 245 may improve the usability of the connector 200 as it is connected or disconnected from a gases delivery system component.

Figure 6:
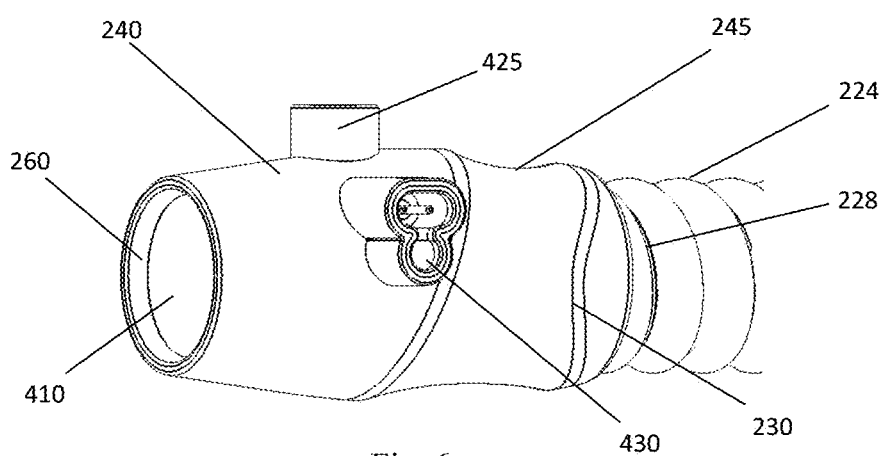
FIG. 6 shows a perspective view of the medical circuit according to the embodiment of FIG. 2.

The overmold 240 may, in some embodiments, form a lip 260 that extends beyond the plurality of rigid components 230, as shown more clearly in FIG. 6. The lip 260 may comprise a flexible tip and may aid the connection between the connector 200 and a gases delivery system component. The connection may be aided due to a chamfered lead-in, which may improve the alignment of the connector 200 with a gases delivery system component.

The plurality of rigid components 230 may be arranged in such a way that the plurality of rigid components 230 form an internal wall having a smooth and continuous transition to the internal wall of the medical tube 220. Thus, areas where dirt or potentially harmful substances may become trapped may be limited or eliminated. This may contribute to the medical circuit 205 being able to be satisfactorily cleaned such that it may be reused. Cleaning mechanisms may include, but are not limited to, soaking and autoclaving. A smooth and continuous internal wall spanning between the medical tube 220 and the connector 200 may also prevent an increase in resistance to flow within the circuit 205.

Figure 4A:
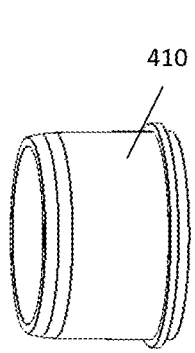
FIGS. 4A, 4B, 4C, and 5 show components of the medical circuit according to the embodiment of FIG. 2.
Figure 4B:
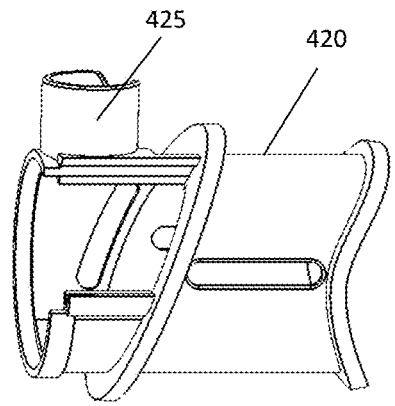
Figure 4C:
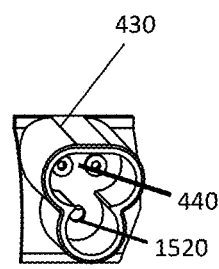

The plurality of rigid components 230 may comprise, for example, a power adaptor port 430, a carrier part 420, and a rigid cuff 410, as shown in more detail in FIGS. 4a, 4b, and 4c. The plurality of rigid components 230 is in no way limited to three rigid components but may, in some embodiments, comprise two or fewer rigid components (inclusive of zero rigid components, for example in an overmolded connector) and, in other embodiments, may comprise four or more rigid components.

The power adaptor port 430 is shown in more detail in FIG. 4C and may facilitate the electrical connection between the connector 200 and an electrical source, thereby providing power to the heating component of the medical tube 220. The electrical source may, in some embodiments, be at least partially associated with a gases delivery system component or it may be a separate apparatus. An external lead may be used to provide the connection between the power adaptor port 430 and the electrical source. Some embodiments may not comprise a heating component within the medical tube 220 and, thus, the connector 200 may not comprise the power adaptor port 430. In other embodiments, multiples of the power adaptor port 430 may be used and associated with the connector 200. In some embodiments, the power adaptor port 430 may be incorporated with another of the plurality of rigid components 230, for example, with the carrier part 420.

The carrier part 420 is shown in more detail in FIG. 4B and may comprise a probe port 425 that can be configured to receive a sensor probe, for example, a temperature probe or a flow probe. In some embodiments, multiples of the probe port 425 may be associated with the connector 200 while, in other embodiments, the connector 200 may not comprise the probe port 425. In some embodiments, the overmold 240 may provide a soft inner surface to a portion of the probe port 425 and/or the power adaptor port 430. Thus, the probe port 425 and/or the power adaptor port 430 may comprise a soft portion to improve the seal between a probe and/or a power adaptor that may be inserted into the probe port 425 and/or the power adaptor port 430, respectively, by compensating for variations that exist in the contacting surfaces. In some embodiments, the overmold 240 comprises an undercut or flexible protrusion 250, as illustrated in FIGS. 2 and 3. The flexible protrusion 250 may comprise an overhanging lip and may be a compressible and sealing protrusion that compensates for surface variations in the probe port 425. The flexible protrusion 250 may be used with the power adaptor port 430 in addition to, or instead of, the probe port 425 and, thus, is not limited to the probe port 425.

The rigid cuff 410 is shown in more detail in FIG. 4A and may be integrated with the medical tube 220 such that the rigid cuff 410 may interact with a port on a gases delivery system component to form a connection between the connector 200 and the gases delivery system component. The rigid cuff 410 may be configured to connect with different medical tapers, for example, but not limited to, a 22 mm tapered cuff. In some embodiments, the rigid cuff 410 may be configured to connect with a female tapered cuff. In other embodiments, the rigid cuff 410 may be configured to connect with a male tapered cuff.

To remove the connector 200, an axial rotational force may be applied to break the taper or friction seal followed by removing the connector 200. The force required to remove the connector 200 following the breaking of the taper seal may, therefore, be lower than other connectors because such force may not be required to break the taper seal. As a result, it may be less difficult to remove the connector 200 than other connectors. The retention force may be maintained such that it is sufficient for the requirements of the gases delivery system 100. The rigid cuff 410 may also provide a substantially constant connection and/or disconnection force between the connector 200 and a gases delivery system component. This force may not be substantially reduced upon wetting of the connector 200. As a result, usability is improved when compared to other connectors because a substantially lower force is needed to form and/or break a connection while reducing failure rates and without impacting the connection between the connector 200 and a gases delivery system component. The rigid cuff 410 may further reduce the impact of side loading of the connector 200, which in other connectors can cause unwanted and/or accidental disconnection at low forces as a result of the elastic and/or flexible cuffs that may be used. This may improve the overall performance and usability of the connector 200.

Figure 5:
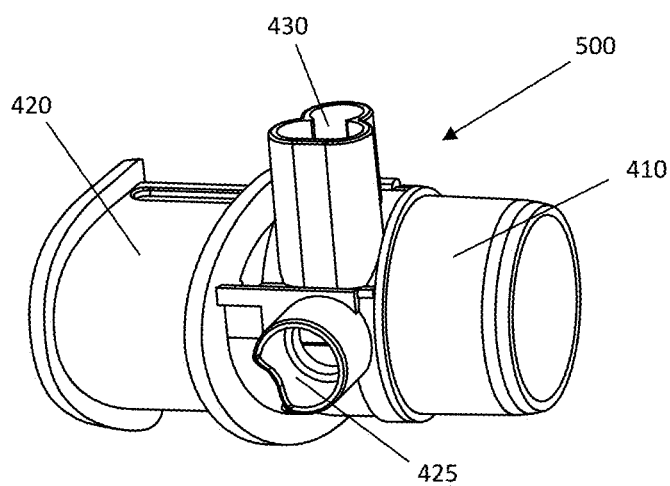

The plurality of rigid components 230 may form at least part of a preassembled structure 500, for example, by clipping the plurality of rigid components 230 into place in preparation for overmolding, as shown in more detail in FIG. 5. In some embodiments, the preassembled structure 500 may be formed from two or more of the plurality of rigid components 230, for example, two or more of the power adaptor port 430, the carrier part 420, and the rigid cuff 410. Any combination of two or more of the plurality of rigid components 230 may be used. The plurality of rigid components 230 provide a lower cost material to fill the bulk of the connector 200, with the overmold 240 being formed around the preassembled structure 500. The thickness of the overmold 240 may be reduced when compared with other connectors, which may reduce the overall manufacturing time due to a reduced cooling time.

In some embodiments, the preassembled structure 500 may comprise a clamp (not shown) to aid with the manufacturing of the connector 200. The clamp may be coupled with the power adaptor port 430 or, in alternative embodiments, may be coupled with other components of the plurality of rigid components 230, for example, the carrier part 420 or the rigid cuff 410. As an example, the clamp may attach to the second elongate member 228 such that it is held in place in relation to the preassembled structure 500 during manufacturing in preparation for the application of the overmold 240. In some embodiments, the clamp may attach to the first elongate member 224.

The materials of the plurality of rigid components 230 and of the overmold 240 may be chosen such that they bond to form the connector 200. The medical tube 220 may also be made from a thermoplastic elastomer that will bond with the connector 200. The bonding may aid in reducing or eliminating the likelihood of separation of the medical tube 220 and the connector 200 over repeated uses, which separation may create dirt traps that may be difficult to clean. The melting point of the material of the medical tube 220 may be comparable to that of the connector 200, such that the medical tube 220 is less likely to be damaged during manufacturing.

Material choice may also take into consideration the feel and appearance of the connector 200, such that it is aesthetically pleasing. Similarly, material choices may comprise materials that maintain this appearance throughout the life of the circuit 205. This is an improvement compared with other reusable circuits, which may discolour as the materials degrade over time and/or in response to the cleaning processes. Use of thermoplastic elastomers may also reduce the overall cost of the connector 200. A simplified embodiment may use glue or adhesive to secure the connector 200 and the medical tube 220 together.

The materials may be chosen such that the overall assembly of the medical tube 220 and the connector 200 can be autoclaved and/or soaked. As a result, the medical circuit 205 may be reused. The medical circuit 205 may last for up to 50 cycles without compromising the condition of the medical tube 220 and the connector 200.

As discussed below, in some embodiments, a vent may be incorporated into the connector 200 and/or the medical tube 220 to allow gases to move into/out of the first elongate member 224 during autoclaving.

In some embodiments, the circuit 205 may comprise an inspiratory tube that extends between a patient interface or wye-piece and a humidification apparatus.

Vent

Autoclaving exposes the medical tube 220 to a large range of pressures and temperatures. Some embodiments include the realization that a vent can advantageously allow air or other gases to move between the lumen of the first elongate member 224 and the atmosphere during autoclaving to prevent the first elongate member 224 from bursting or collapsing, which would cause the medical tube 220 to become unsightly and diminish the insulating properties of the first elongate member 224. In some embodiments, a vent is inserted directly or indirectly into the first elongate member 224 to prevent the lumen of the first elongate member 224 from bursting or collapsing during autoclaving. The vent allows a gases pathway between the lumen of the first elongate member 224 and the atmosphere. Indirect insertion of the vent involves a housing that maintains gaseous communication between the lumen of the first elongate member 224 and the vent.

The vent can comprise a material with a low surface tension to discourage liquid and/or substances from entering the lumen of the first elongate member 224 during soakage. Liquid and/or substance ingress may cause the first elongate member 224 to become unsightly and heavy, which may increase patient discomfort. In an embodiment, the vent can comprise a hole through which gases can flow. A cap seals the hole to prevent liquid and/or substances from entering the lumen of the first elongate member 224 during soakage.

Figure 7:
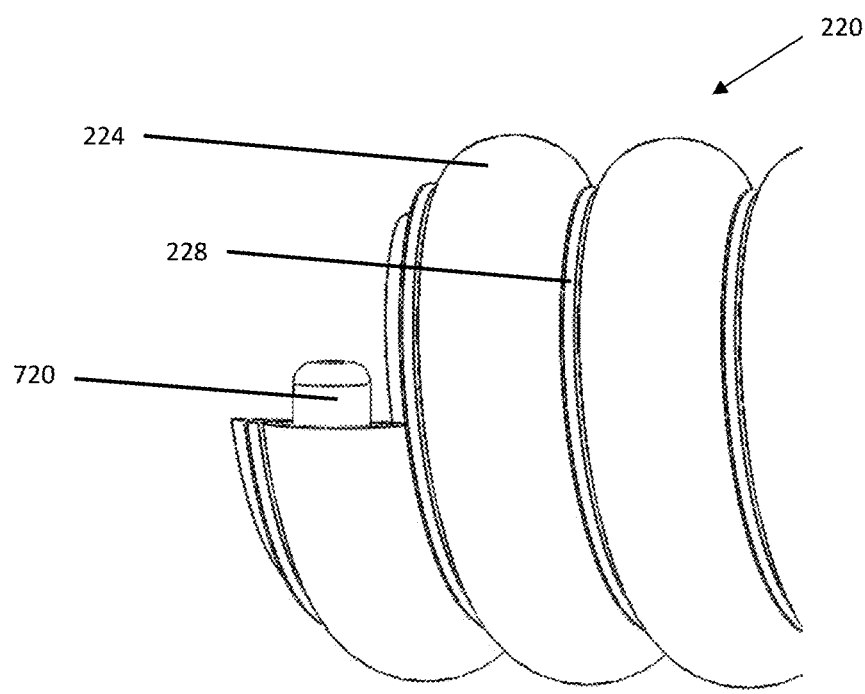
FIGS. 7 and 8 show perspective views of a medical tube comprising a vent according to an embodiment of the present disclosure.

FIG. 7 shows an embodiment of the medical tube 220 for use within a gases delivery system. The medical tube 220 comprises the first elongate member 224 and the second elongate member 228. The first elongate member 224 is hollow, thus comprising a lumen, that provides thermal insulation to the medical tube 220. This improves the flexibility and humidity performance of the medical tube 220 when compared with other medical tubes. The first elongate member 224 comprises a vent 720. The second elongate member 228 provides reinforcement to the medical tube 220. The second elongate member 228 comprises a plurality of heater wires (not shown) to heat the medical tube 220.

Figure 8:
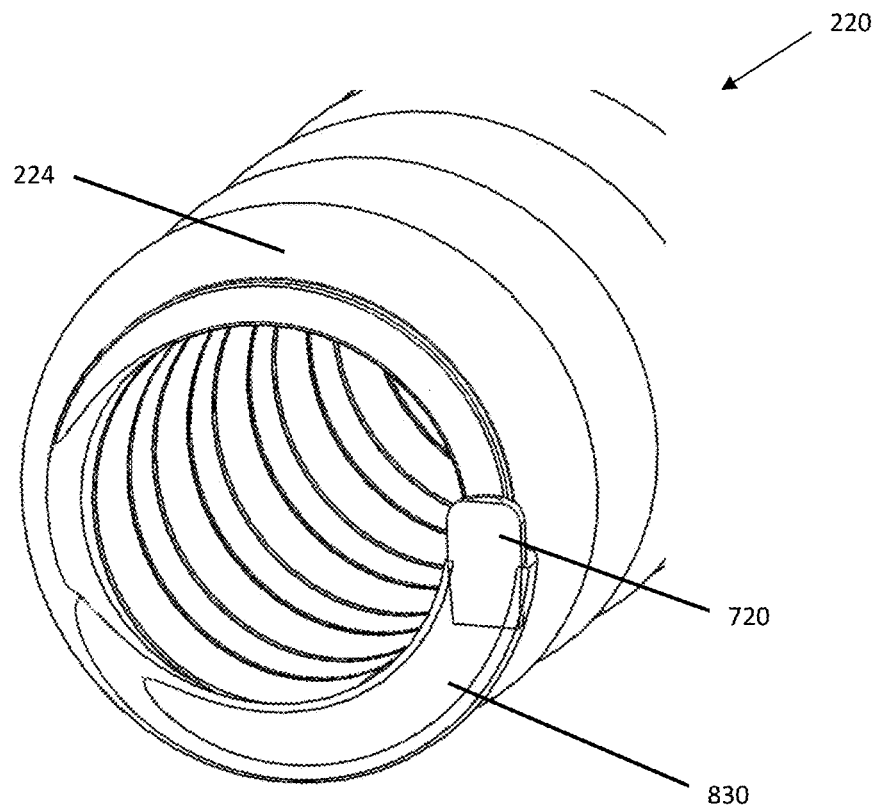

FIG. 8 shows that the vent 720 can be inserted into a lumen 830 of the first elongate member 224. At least a portion of the vent 720 protrudes from the lumen 830 of the first elongate member 224. In an embodiment, the vent 720 can be fully inserted into the lumen 830 of the first elongate member 224 so that it does not protrude from the lumen 830.

Figure 9:
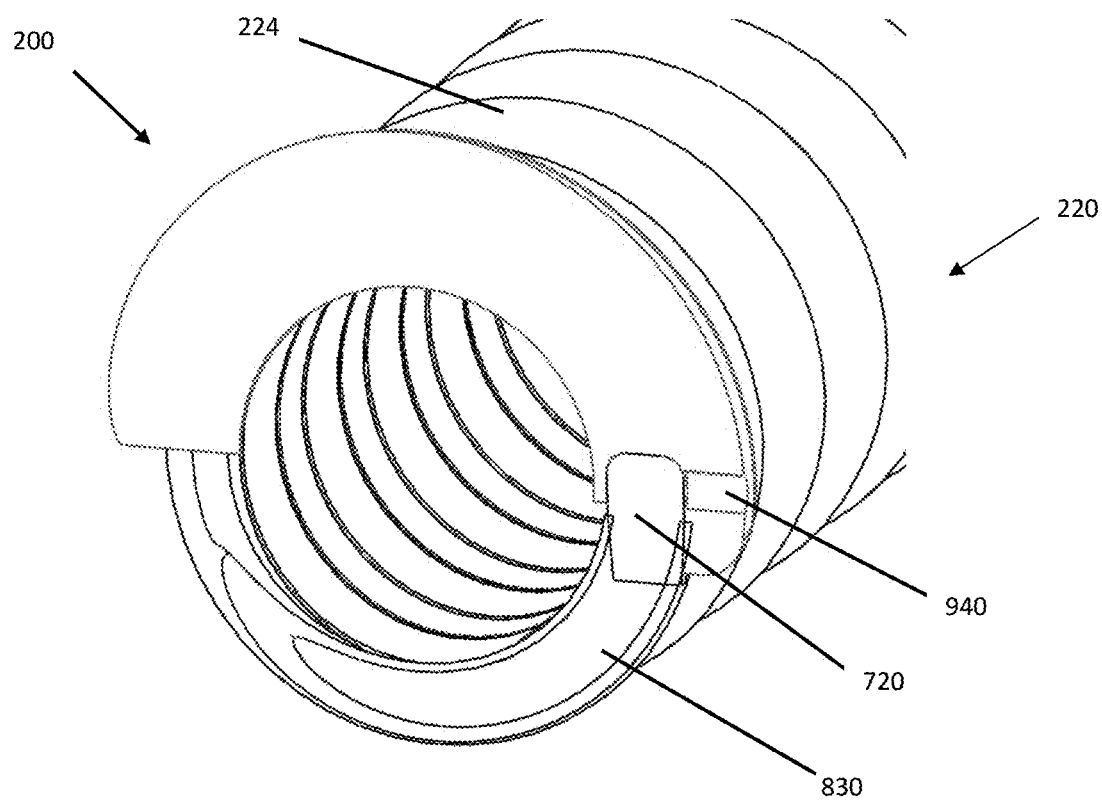
FIGS. 9, 10, and 11 show perspective views of a medical circuit comprising a vent according to an embodiment of the present disclosure.

An embodiment of the connector 200 is overmolded onto the medical tube 220 as shown in more detail in FIG. 9. In some embodiments, a pin may be inserted during the molding process to maintain a gases pathway 940 between the lumen 830 of the first elongate member 224 and the atmosphere. The vent 720 is positioned within the gases pathway 940. This embodiment provides a simple option for inserting the vent 720 into the lumen 830 of the first elongate member 224.

Figure 10:
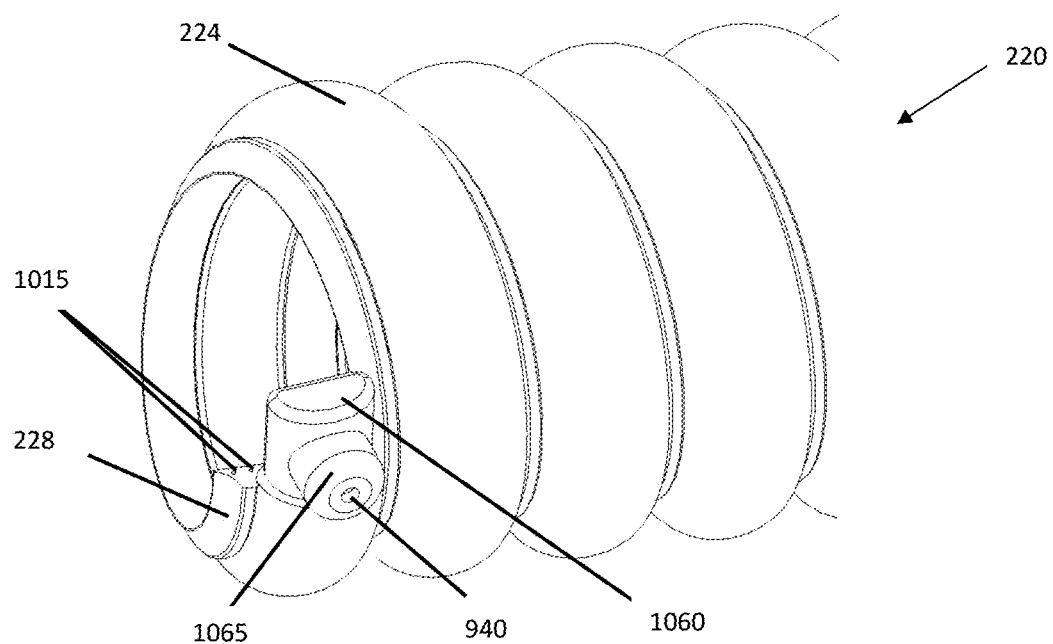

FIG. 10 shows that the second elongate member 228 comprises a plurality of heater wires 1015 to heat the medical tube 220. In the illustrated embodiment, the plurality of heater wires 1015 comprises two heater wires. The plurality of heater wires 1015 may function to at least partially heat the medical tube 220, which reduces or eliminates condensate within the medical tube 220. In an embodiment, the second elongate member 228 can comprise one or more sensing wires. In an embodiment, the second elongate member 228 can comprise a combination of sensing and heater wires. FIG. 10 further illustrates an embodiment wherein the first elongate member 224 comprises a housing 1060. The housing 1060 protrudes out of the first elongate member 224. In the illustrated embodiment, the housing 1060 may be at least partially inserted into the first elongate member 224. In some embodiments, the housing 1060 may be fully inserted into the first elongate member 224. The housing 1060 comprises a vent housing 1065 that provides the gases pathway 940 between the first elongate member 224 and the atmosphere.

Figure 11:
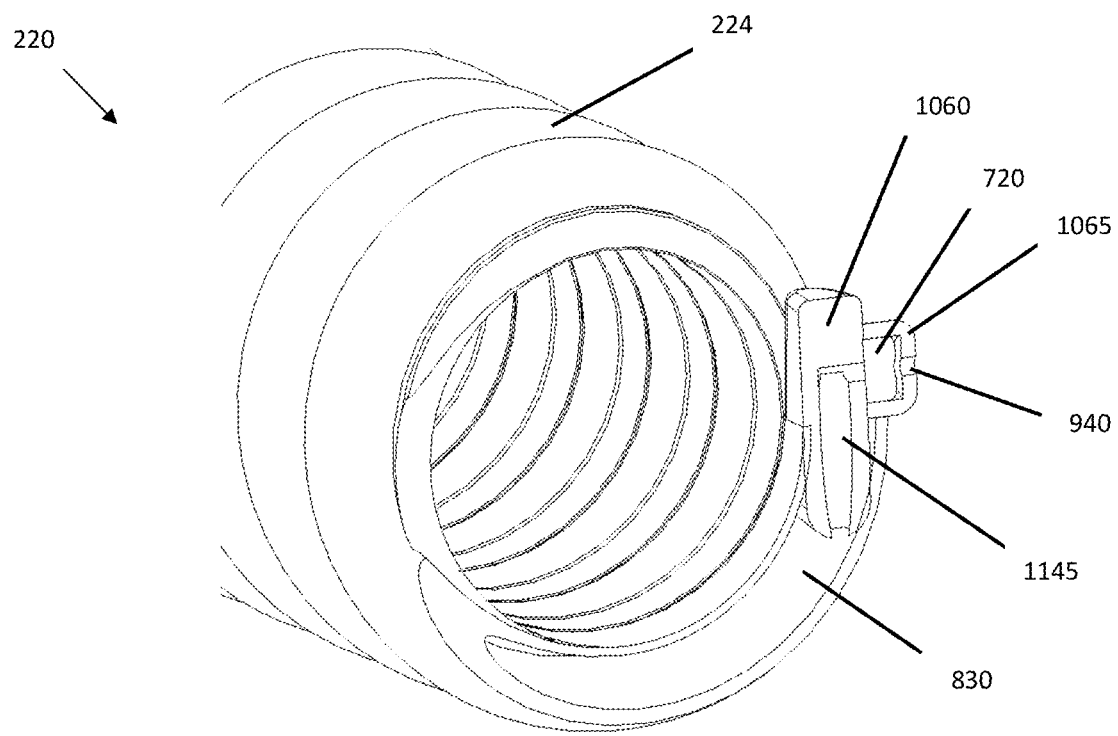

FIG. 11 shows a cross-section of the housing 1060 comprising the vent 720, inserted in the vent housing 1065. The vent housing 1065 inserts into the lumen 830 of the first elongate member 224. The gases pathway 940 creates a path for gases to flow from the lumen 830 of the first elongate member 224, through an inner pathway 1145, through the vent 720 to the atmosphere. The housing 1060 is simple to insert during assembly. The housing 1060 protects the vent 720 during overmolding and better secures the vent 720 in the connector. The housing 1060 reduces the likelihood of the vent 720 acting as a dirt trap.

Figure 12:
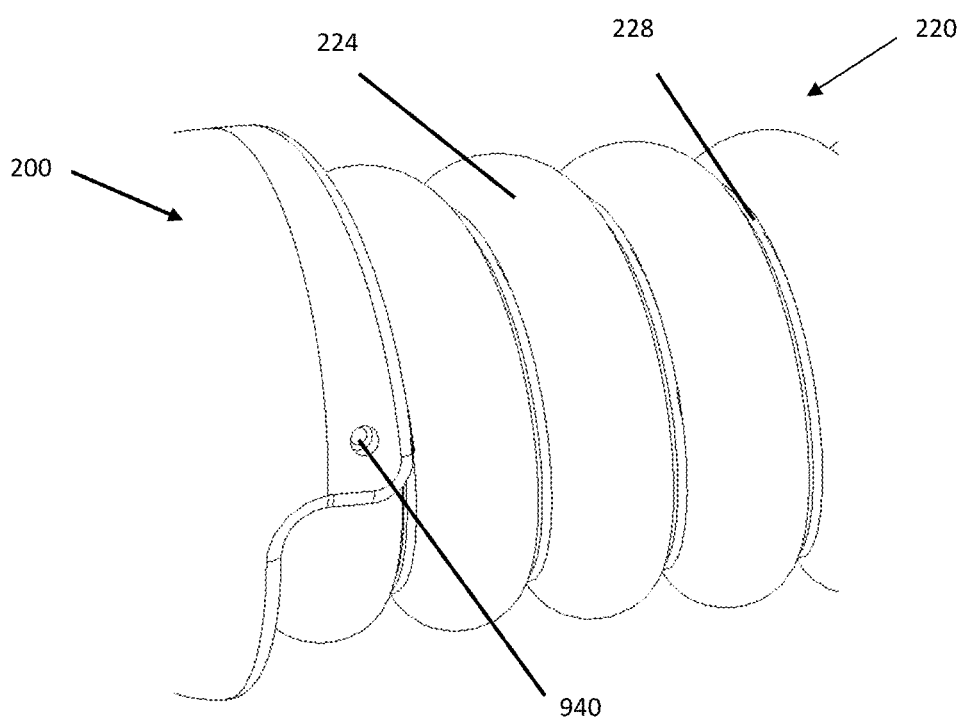
FIG. 12 shows a perspective view of a medical circuit according to an embodiment of the present disclosure.

FIG. 12 shows an embodiment of the connector 200 that is overmolded onto the medical tube 220. A pin can be inserted into the connector 200 during the molding process to maintain the gases pathway 940 between the first elongate member 224 and the atmosphere.

Figure 13:
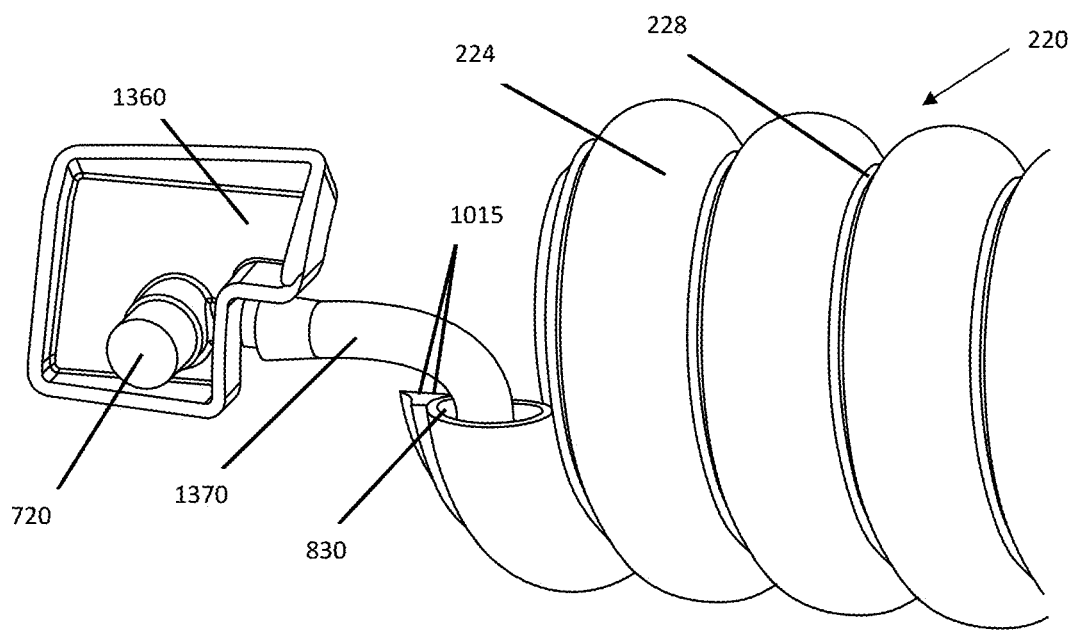
FIG. 13 shows a perspective view of a medical circuit comprising a vent according to an embodiment of the present disclosure.

FIG. 13 shows an embodiment where the vent 720 is pneumatically connected to the lumen 830 of the first elongate member 224 via an inner conduit 1370. Thus, the lumen 830 of the first elongate member 224 is in gaseous communication with the atmosphere. A housing 1360 comprises the vent 720. The housing 1360 is configured to be attached to a connector (not shown). In an embodiment, the connector comprises an electrical connector. The plurality of heater wires 1015 from the second elongate member 228 can be connected to the housing 1360. The housing 1360 may protect the vent 720 from dirt. The housing 1360 can be fully incorporated into the connector. The housing 1360 may comprise an area configured to receive the vent 720. The connector may be overmolded onto the medical tube 220 such that gaseous communication is maintained between the lumen 830 of the first elongate member 224 and the atmosphere, via the vent 720.

Figure 14:
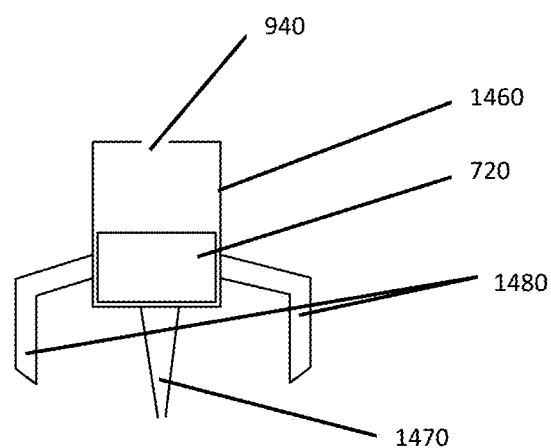
FIG. 14 shows a front sectional view of a vent comprising a housing according to an embodiment of the present disclosure.

FIG. 14 shows an embodiment wherein the vent 720 comprises a housing 1460 that can attach to the first elongate member 224 via an attachment mechanism 1480. In some embodiments, the attachment mechanism 1480 may comprise adhesives, a ring, a strap, clips, any combination of these, or any other suitable attachment mechanism. The attachment mechanism 1480 partially encircles the first elongate member 224 to secure the housing 1460 to the medical tube 220. In an embodiment, the attachment mechanism 1480 may completely encircle the first elongate member 224 to secure the housing 1460 to the medical tube 220.

A piercing member 1470 can be configured to pierce the first elongate member 224, forming the gases pathway 940 between the first elongate member 224 and the atmosphere. In the illustrated embodiment, the gases pathway 940 comprises an opening, for example a hole or slit, in the housing 1460.

In some embodiments, the housing 1460 may not comprise the vent 720. For example, the housing 1460 may be empty. Thus, to enable soaking of the medical tube 220, the housing 1460 may comprise a cap.

Figure 15:
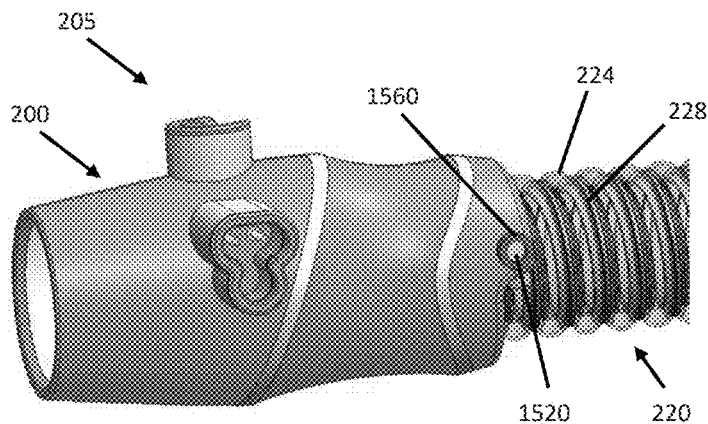
FIG. 15 shows a perspective view of a medical circuit according to an embodiment of the present disclosure.

FIG. 15 shows an embodiment of the medical circuit 205 wherein the connector 200 comprises a vent 1520 within a housing 1560, wherein the vent 1520 provides gaseous communication between the first elongate member 224 and the atmosphere. The housing 1560 can protrude at least partially into the first elongate member 224 of the medical tube 220. In an embodiment, the connector 200 can be overmolded onto the medical tube 220 and at least a part of the housing 1560. In an embodiment, the housing 1560 protrudes completely into the first elongate member 224.

The vent 1520 comprises a thin film component; for example, the vent 1520 may be between 1 μm and 1 mm thick. In an embodiment, the vent 1520 may be 130 μm thick. This allows for a high flow rate of gases through the vent 1520. The size of the vent 1520 provides an aesthetically pleasing product as it can be incorporated easily and seamlessly into the connector 200. The vent 1520 can comprise polytetrafluoroethylene (PTFE) and/or other materials suitable to resist liquid and/or substance ingress while maintaining permeability to gases. In the illustrated embodiment, the vent 1520 comprises a non-woven hydrophobic film; in another embodiment, the vent 1520 may comprise a woven hydrophilic film. In an embodiment, the vent 1520 may be oleophobic. The vent 1520 can withstand rigorous cleaning processes, such as autoclaving, pasteurizing, and soaking. The integrity of the vent 1520 may be maintained during soaking under pressure up to 1 meter head of water.

Figure 16:
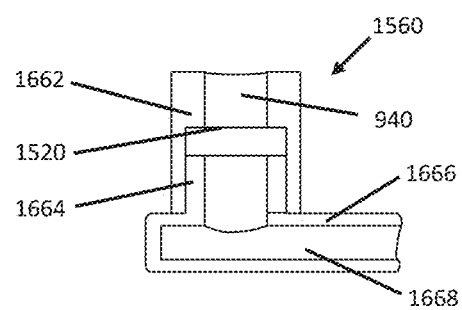
FIG. 16 shows a cross-sectional view of a housing according to the embodiment of FIG. 15.

FIG. 16 shows an embodiment of the housing 1560 that comprises a plug 1662, a receiving portion 1664, and a pipe 1666. In an embodiment, the housing 1560 can comprise a cap. The vent 1520 fits between the plug 1662 and the receiving portion 1664. The plug 1662 and the receiving portion 1664 each comprises an annular ring, with an opening to allow the gases pathway 940 to be formed between the first elongate member 224 of the medical tube 220 and the atmosphere. The vent 1520 bridges the gases pathway 940 to provide a barrier to liquid and/or substance ingress into the first elongate member 224. As high gases flow rates are enabled through the vent 1520, the diameter of the exposed region of the vent 1520 can be small. The diameter of the exposed region of the vent 1520 can be, for example, 3 mm. This reduces the likelihood of physical damage to the vent 1520, for example in the form of punctures, dirt or substances reacting with or occluding the gases pathway 940, and is aesthetically pleasing. In an alternative embodiment, the diameter of the exposed region of the vent 1520 can be larger to facilitate higher gases flow through the vent 1520. In an embodiment, the cap can be configured to close the gases pathway 940 when the vent 1520 is not in use. In an embodiment, the exposed region of the vent 1520 may comprise a square or rectangular cross-section, or another shape appropriate to the application.

Figure 17:
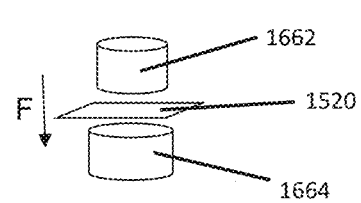
FIG. 17 shows an exploded view of a housing according to the embodiment of FIG. 15.

FIG. 17 shows an exploded view of the housing 1560, illustrating a way to assemble the vent 1520 with the plug 1662 and the receiving portion 1664. The plug 1662 can be used to apply a force to push the vent 1520 into place in the housing 1560, in the direction as indicated by the arrow F.

The plug 1662 is therefore received by the receiving portion 1664, and the vent 1520 is firmly placed within the housing 1560. This reduces the vulnerability of the vent 1520 to damage as discussed, and also to accidental repositioning which may compromise the performance of the system. For example, if the vent 1520 moves during cleaning, liquid and/or substances may enter the first elongate member 224, which may discolor or compromise the integrity of the first elongate member 224. In some embodiments, the vent 1520 may be held in place by clips, a latch, friction fit, or adhesives, or may be overmolded into place.

In an embodiment, the pipe 1666 and the receiving portion 1664 are a single component. The plug 1662 and the vent 1520 are assembled directly onto this component. In an alternative embodiment, the plug 1662 and the receiving portion 1664 are preassembled with the vent 1520 before being coupled with the pipe 1666. In this embodiment, the pipe 1666 may comprise a region that receives the preassembled configuration. Coupling between the plug 1662 and the receiving portion 1664 can be achieved using a friction fit, adhesives, a latch, clips, welding, or overmolding.

The pipe 1666 comprises a channel 1668 that continues the gases pathway 940 between the atmosphere and the first elongate member 224 of the medical tube 220. The gases pathway 940 continues from the pipe 1666 through the receiving portion 1664 and the plug 1662 to the atmosphere. This provides a path through which gases can flow during cleaning, such as during autoclaving. The gases pathway 940 reduces or eliminates the likelihood of the first elongate member 224 being compromised during cleaning. The channel 1668 can be set at any angle from the receiving portion 1664. The size of the channel 1668 can be optimised to provide sufficient gases flow between the first elongate member 224 and the atmosphere. The pipe 1666 can be inserted into the first elongate member 224 of the medical tube 220. Thus, the pipe 1666 forms a pneumatic connection between the atmosphere and the first elongate member 224. This is shown in more detail in FIG. 18.

With reference again to FIG. 17, the plug 1662 and the receiving portion 1664 interact via a friction fit. In an embodiment, the plug 1662 protrudes into the receiving portion 1664. In an embodiment, the receiving portion 1664 protrudes into the plug 1662. The plug 1662 and the receiving portion 1664 are shown to be substantially cylindrical in shape. In some embodiments, the shape may be customised to the application, for example, a rectangular shape may be used. In the illustrated embodiment, the gases pathway 940 and the channel 1668 are each shown to comprise substantially straight segments, however it is to be understood that the gases pathway 940 and the channel 1668 may each be curved or comprise bends depending on the configuration of the housing 1560.

Figure 18:
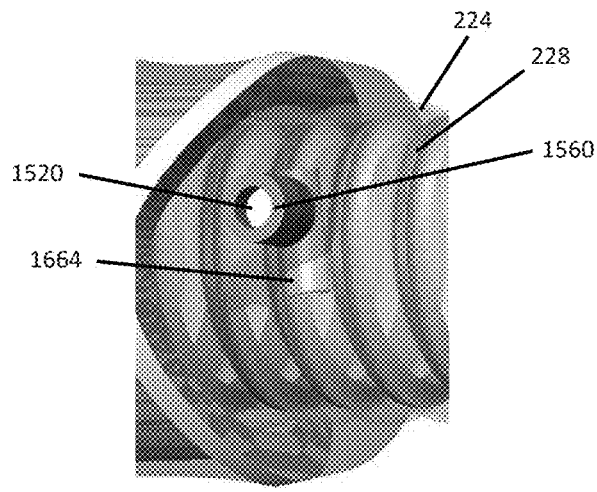
FIG. 18 shows a perspective view of a medical circuit according to the embodiment of FIG. 15.

FIG. 18 shows the connector 200 comprising the housing 1560. The housing 1560 protrudes into the first elongate member 224 to form a pneumatic connection between the channel 1668 and the first elongate member 224. An opening may be formed in the first elongate member 224 to receive the housing 1560. In an embodiment, the housing 1560 may be pushed into the opening of the first elongate member 224. In an embodiment, the housing 1560 can be inserted at the termination of the first elongate member 224.

In some embodiments, the vent 1520 can be combined with the embodiments shown in either one of FIG. 13 or 14. With reference to FIG. 13, the vent 1520 can be coupled with the housing 1360 by way of a mechanical fit or adhesives. The inner conduit 1370 forms a pneumatic connection between the first elongate member 224 and the atmosphere.

With reference to FIG. 14, the vent 1520 can be coupled with the housing 1460. For example, the vent 1520 can seal the gases pathway 940 from liquid or dirt ingress. As discussed, the vent 1520 allows gaseous communication between the first elongate member 224 and the atmosphere via the gases pathway 940.

The vent 1520 also can be integrated into the power adaptor port 430. The power adaptor port 430 can comprise multiple lobes. In the example shown in FIG. 4C, the power adaptor port 430 comprises three lobes, such that the power adaptor port 430 resembles a cloverleaf when viewed from above. Pins 440 can be placed in two of the lobes to facilitate an electrical connection. Preferably, the pins 440 are solid, rather than hollow. Solid pins are more durable and robust than hollow pins. Solid pins can also ease manufacturing of the connector 200. For example, the pins 440 being hollow can allow the overmold 240 to enter the pins 440 during manufacturing. The vent 1520 can be located in the unused lobe of the power adaptor port 430. The vent 1520 allows the first elongate member 224 to communicate with the atmosphere. Preferably, the vent 1520 diameter is 5 mm or thereabout to fit within the power adaptor port 430.

Figure 19A:
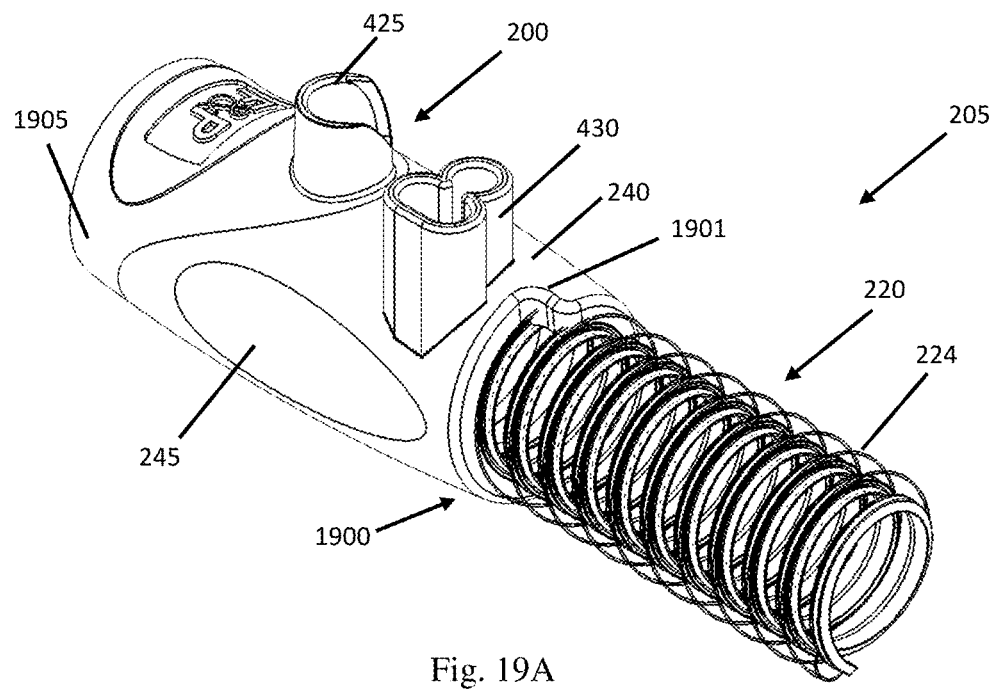
FIG. 19A shows an isometric view of a medical circuit according to an embodiment of the present disclosure.
Figure 19B:
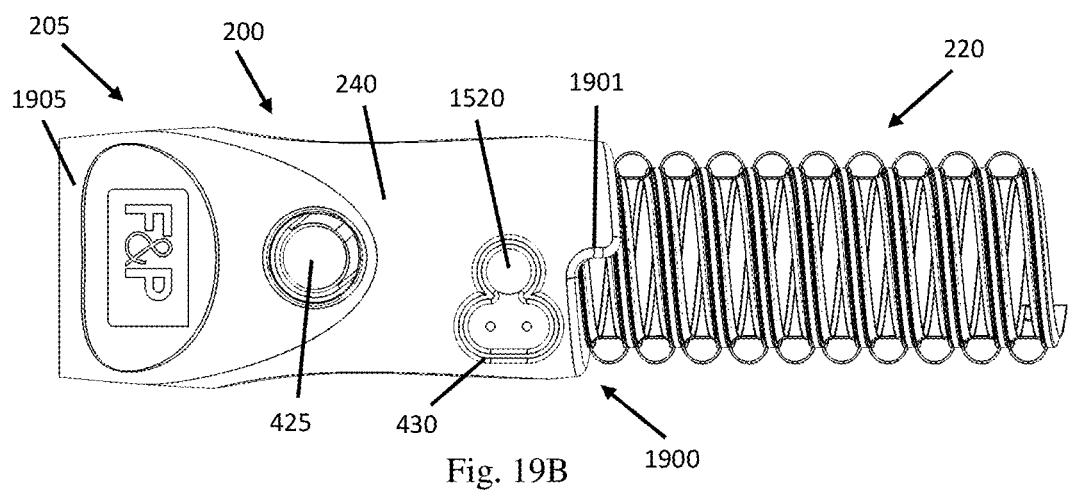
FIG. 19B shows a top plan view of the medical circuit according to the embodiment of FIG. 19A.
Figure 19C:
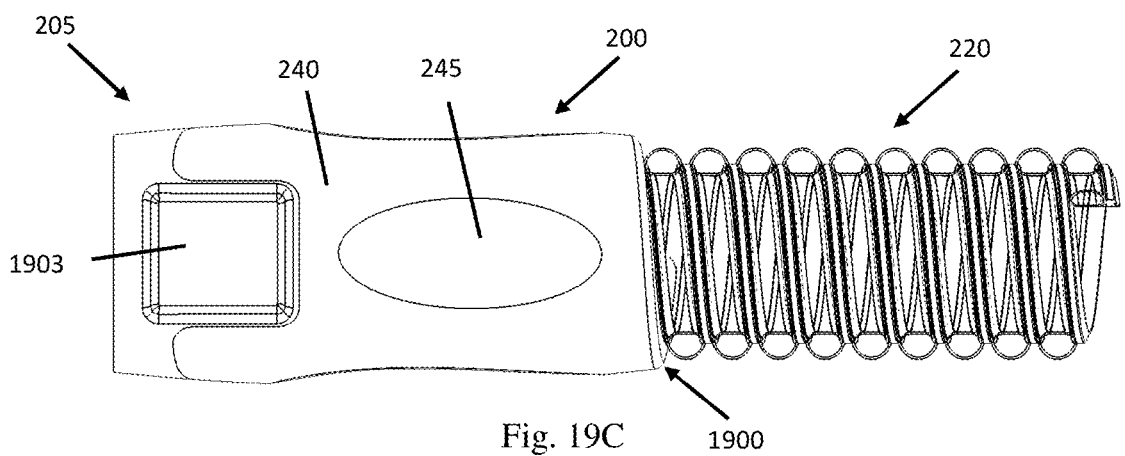
FIG. 19C shows a bottom plan view of the medical circuit according to the embodiment of FIG. 19A.

Generalized FIG. 19 shows the medical circuit 205 according to an embodiment of the present disclosure. FIG. 19A shows an isometric view of the medical circuit 205. FIG. 19B shows a top plan view of the medical circuit 205. FIG. 19C shows a bottom plan view of the medical circuit 205. The medical circuit 205 comprises the connector 200 and the medical tube 220. The connector 200 comprises a non-overmolded taper 1905 and the overmold 240. Generally nonreactive materials such as polypropylene are suitable for the taper 1905. Preferably, the material selected for the taper 1905 is more rigid than the overmold 240. Rigid materials for the taper 1905 were discovered to improve the connection between the connector 200 and other medical equipment. The connector 200 comprises the probe port 425 and the power adaptor port 430. In the embodiment of FIG. 19A, the probe port 425 is within the region of the taper 1905. The power adaptor port 430 is within the area covered by the overmold 240. As discussed below, a vent is incorporated in the power adaptor port 430 to allow gaseous communication between the first elongate member 224 and the atmosphere through the unused lobe. Due to the lower melt flow index of the overmold 240, the rigid parts (namely the probe port 425, the power adaptor port 430, and the taper 1905) are coupled during overmolding.

An example of the probe port 425 including a notch or fixed locating depression is described in U.S. Pat. No. 7,263,994, which is incorporated herein by reference. The embodiment of FIG. 19A is advantageous because the probe port 425 and the power adaptor port 430 are located in the same plane, for example on top of the connector 200. This configuration can be desirable because it allows for the gripping region 245 on the sides and bottom of the connector 200 to be large. In this example, the probe port 425 and the power adaptor port 430 are in the range of 19 and 20 mm apart or thereabout. One or both of the gripping regions 245 on the sides of the connector 200 can be formed with a flat area for a thumb. Such a configuration can intuitively indicate to the user that the connector 200 should be twisted for removal and not pulled.

The overmold 240 comprises an edge 1900 formed by a shutoff tool during molding. The edge 1900 optionally comprises an offset portion 1901. The offset portion 1901 allows the remainder of the edge 1900 to follow the helical orientation of the first elongate member 224. It was realized that use of such an offset portion 1901 can improve bonding of the overmold 240 to the medical tube 220, particularly to the second elongate member 228 of the medical tube 220.

An identification region 1903 optionally can be included within the taper 1905. The identification region 1903 can be indented. The identification region 1903 can include, for example, markings such as a suitable QR code. Desirably, the identification region 1903 is not overmolded, to improve readability of any such markings.

Modifications described elsewhere in this disclosure can be incorporated in the embodiments of generalized FIG. 19.

Figure 20A:
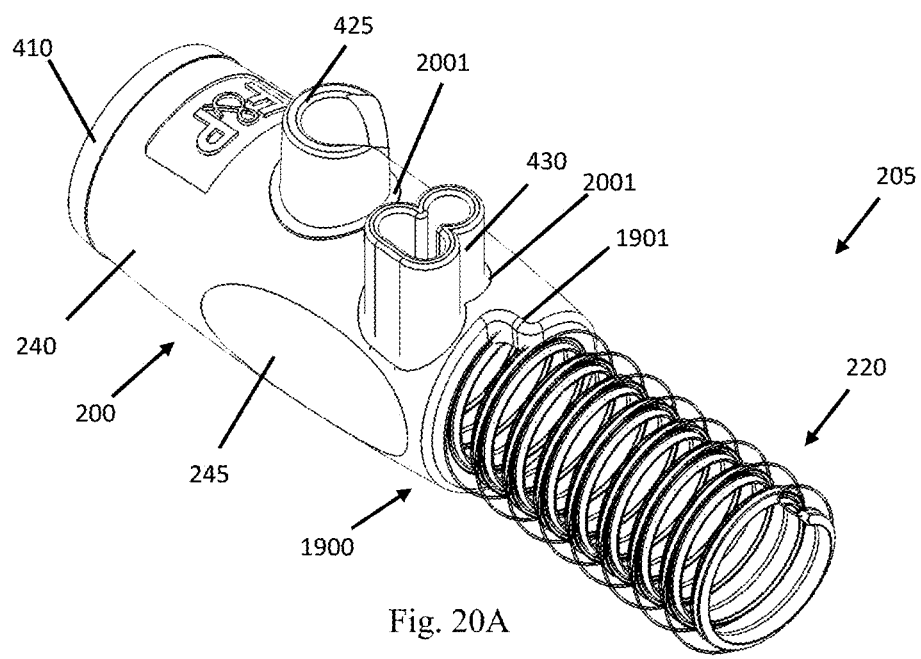
FIG. 20A shows an isometric view of a medical circuit according to an embodiment of the present disclosure.
Figure 20B:
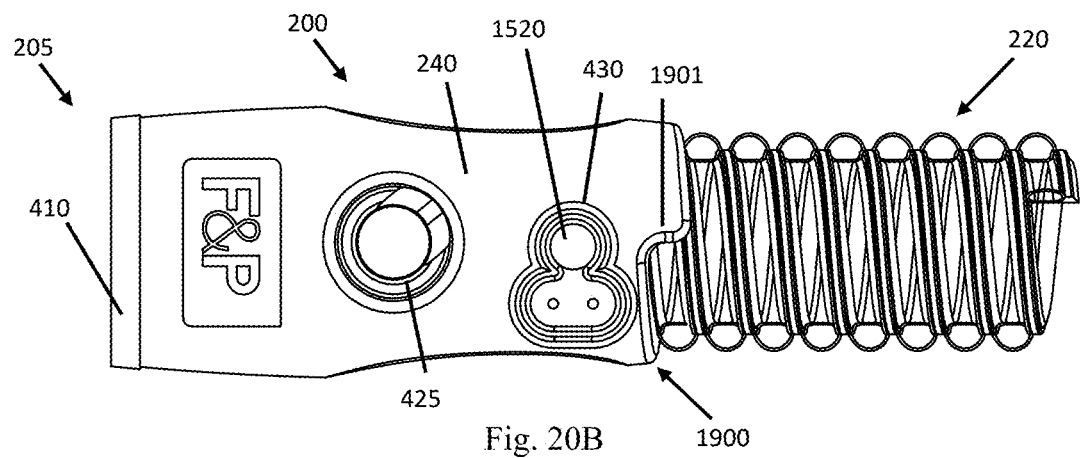
FIG. 20B shows a top plan view of the medical circuit according to the embodiment of FIG. 20A.
Figure 20C:
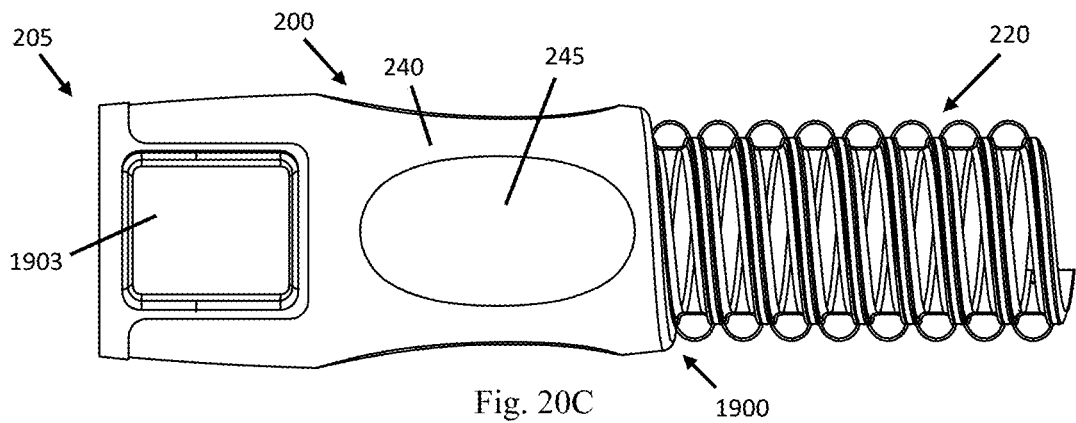
FIG. 20C shows a bottom plan view of the medical circuit according to the embodiment of FIG. 20A.

Generalized FIG. 20 shows the medical circuit 205 according to an embodiment of the present disclosure. FIG. 20A shows an isometric view of the medical circuit 205. FIG. 20B shows a top plan view of the medical circuit 205. FIG. 20C shows a bottom plan view of the medical circuit 205. The medical circuit 205 comprises the connector 200 and the medical tube 220. The features of the medical circuit 205 of generalized FIG. 20 are similar to those of the medical circuit 205 of generalized FIG. 19, and the discussion of generalized FIG. 19 is incorporated by reference. The connector 200 of generalized FIG. 20 includes the rigid cuff 410, without the non-overmolded taper 1905. In the embodiment of generalized FIG. 20, the overmold 240 covers a larger portion of the connector 200 in than in generalized FIG. 19. The larger portion of the connector 200 covered by the overmold 240 can be desirable because it can give more even wall sections which can lead to more stable dimensions. Suitable materials for the rigid cuff 410 include those described with relation to generalized FIG. 4 and FIG. 19.

In the embodiment of generalized FIG. 20, the probe port 425 and the power adaptor port 430 are in the range of 19 and 20 mm apart or thereabout. A protrusion 2001 surrounds each of the probe port 425 and the power adaptor port 430. The protrusion 2001 extends above the overmold 240. Suitable materials for the protrusion 2001 include polypropylene and/or materials described with relation to generalized FIGS. 4 and 19 for the rigid cuff 410 and the taper 1905. The protrusion 2001 can prevent the overmold 240 from flowing onto sides of the components during overmolding. In an embodiment, the protrusion 2001 surrounds the probe port 425 but not the power adaptor port 430. In an embodiment, the protrusion 2001 surrounds the power adaptor port 430 but not the probe port 425.

Modifications described elsewhere in this disclosure can be incorporated in the embodiments of generalized FIG. 20.

Figure 21A:
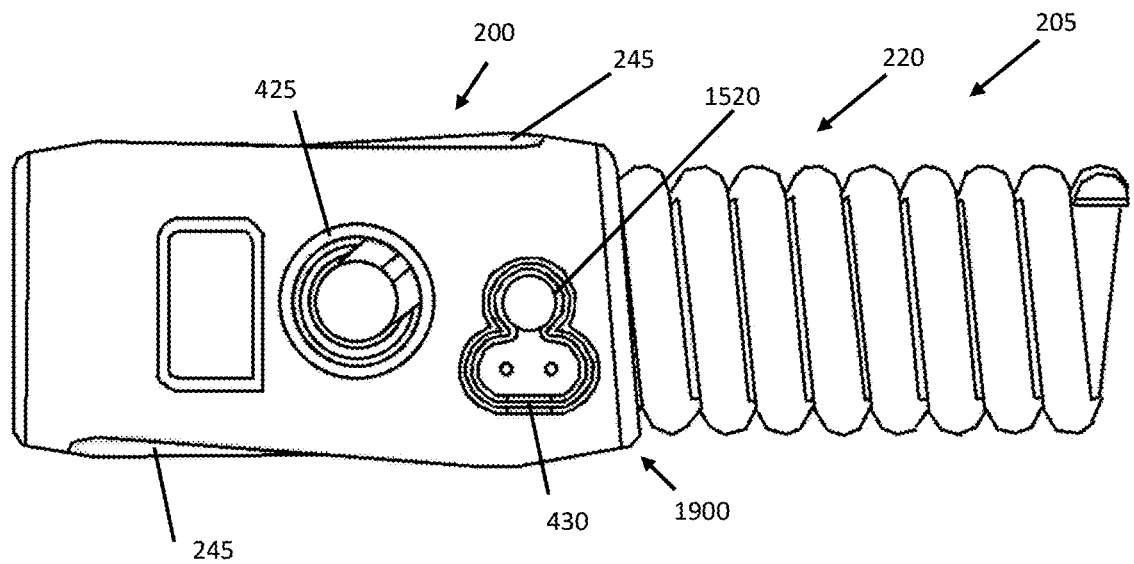
FIG. 21A shows a top plan view of a medical circuit according to an embodiment of the present disclosure.
Figure 21B:
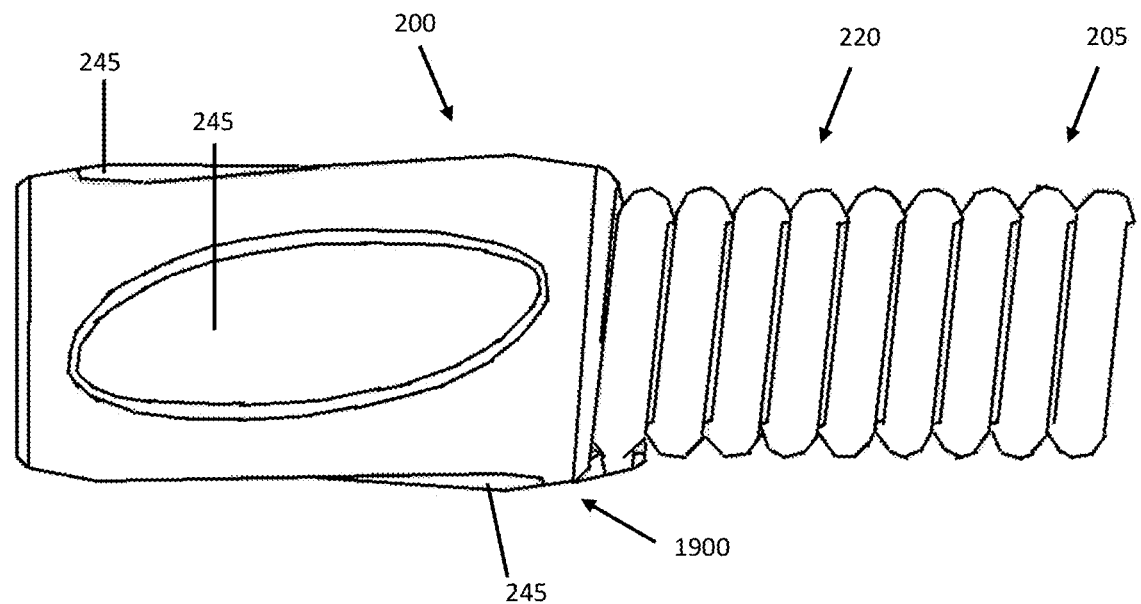
FIG. 21B shows a bottom plan view of the medical circuit according to the embodiment of FIG. 21A.

Generalized FIG. 21 shows the medical circuit 205 according to an embodiment of the present disclosure. FIG. 21A shows a top plan view of the medical circuit 205. FIG. 21B shows a bottom plan view of the medical circuit 205. The medical circuit 205 comprises the connector 200 and the medical tube 220. The features of the medical circuit 205 of generalized FIG. 21 are similar to those of the medical circuit 205 of generalized FIGS. 19 and 20, and the discussions of generalized FIGS. 19 and 20 are incorporated by reference. In the embodiment of generalized FIG. 21, the distance between the probe port 425 and the power adaptor port 430 is 15 mm or thereabout. The configuration of generalized FIG. 21 can be desirable because the probe port 425 and the power adaptor port 430 are in the same plane, allowing for the gripping regions 245 to be increased.

Modifications described elsewhere in this disclosure can be incorporated in the embodiments of generalized FIG. 21.

Generalized FIG. 22 shows the power adaptor port 430 of at least one embodiment of the present disclosure in greater detail. FIG. 22A shows a side perspective view of the power adaptor port 430. FIG. 22B shows a top perspective view of the power adaptor port 430. FIG. 22C shows a bottom perspective view of the power adaptor port 430. FIG. 22D shows a side cross-sectional view of the power adaptor port 430. FIG. 22E shows another side cross-sectional view of the power adaptor port 430. FIG. 22F shows a top plan view of an alternate embodiment of the connector 200 incorporating the power adaptor port 430. FIG. 22G shows a cross-sectional, bottom plan view of the connector 200. The power adaptor port 430 of generalized FIG. 22 can be incorporated in the connector 200 configurations of generalized FIGS. 2, 15, 19, 20, and 21 and other connector configurations described herein.

The power adaptor port 430 of generalized FIG. 22 comprises the vent 1520 in the unused lobe. In some embodiments, the diameter of the vent 1520 is 5 mm or thereabout. The size of the vent 1520 can be selected to compensate for the diameter and/or the length of the gas path described below. The vent 1520 allows gases to move between the first elongate member 224 of the medical tube 220 and the atmosphere during autoclaving.

The power adaptor port 430 comprises an inner conduit 2201. In use, the inner conduit 2201 is inserted in the first elongate member 224 of the medical tube 220. The inner conduit 2201 keeps the first elongate member 224 open and forms part of the gases pathway 940 (not shown in generalized FIG. 22) between the first elongate member 224 and the atmosphere. The vent 1520 comprises a membrane 2203. The membrane 2203 can be overmolded into and span the unused lobe of the power adaptor port 430. A vent path 2205 extends between the inner conduit 2201 and the membrane 2203 and also forms part of the gases pathway 940.

Figure 22A:
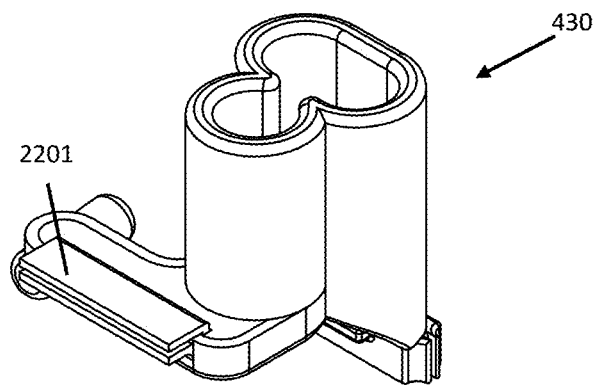
FIG. 22A shows a side perspective view of a power adaptor port according to an embodiment of the present disclosure.
Figure 22B:
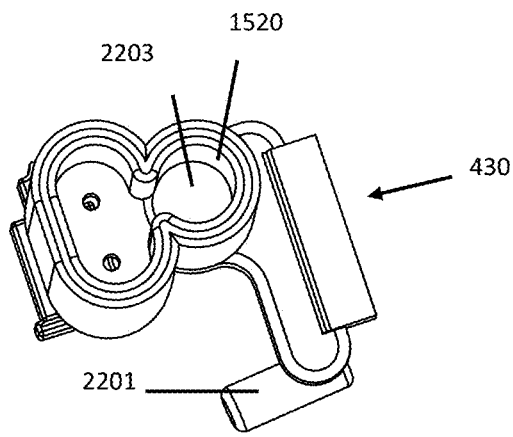
FIG. 22B shows a top perspective view of the power adaptor port according to the embodiment of FIG. 22A.
Figure 22C:
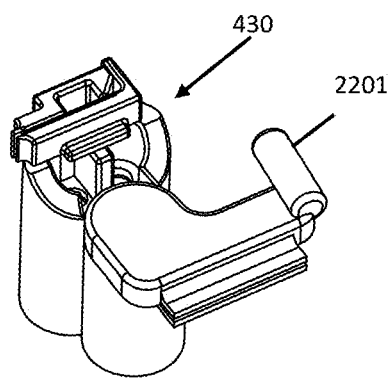
FIG. 22C shows a bottom perspective view of the power adaptor port according to the embodiment of FIG. 22A.
Figure 22D:
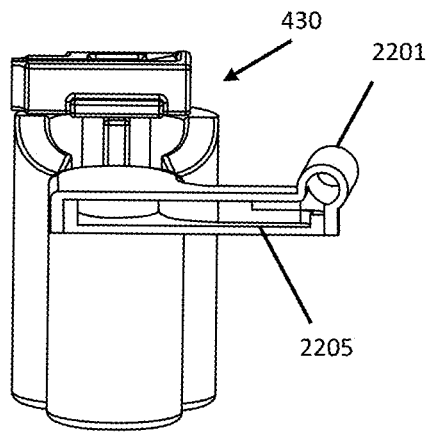
FIG. 22D shows a side cross-sectional view of the power adaptor port according to the embodiment of FIG. 22A.
Figure 22E:
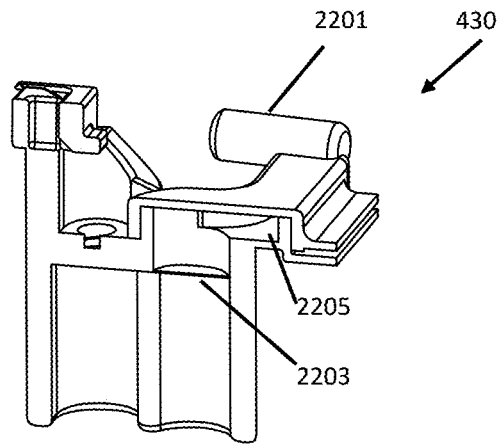
FIG. 22E shows another side cross-sectional view of the power adaptor port according to the embodiment of FIG. 22A.
Figure 22F:
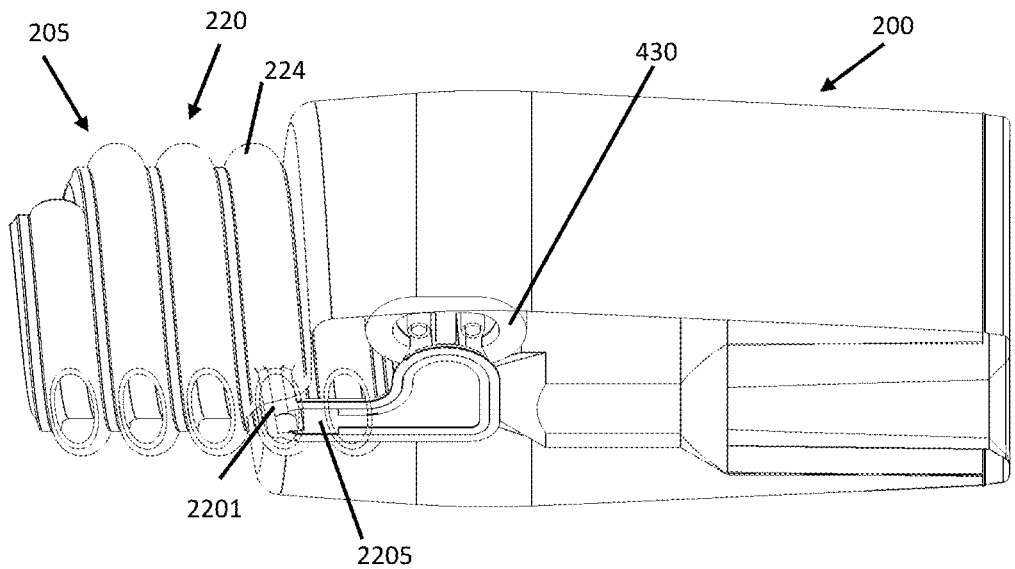
FIG. 22F shows a top plan view of a medical circuit incorporating the power adaptor port according to the embodiment of FIG. 22A.
Figure 22G:
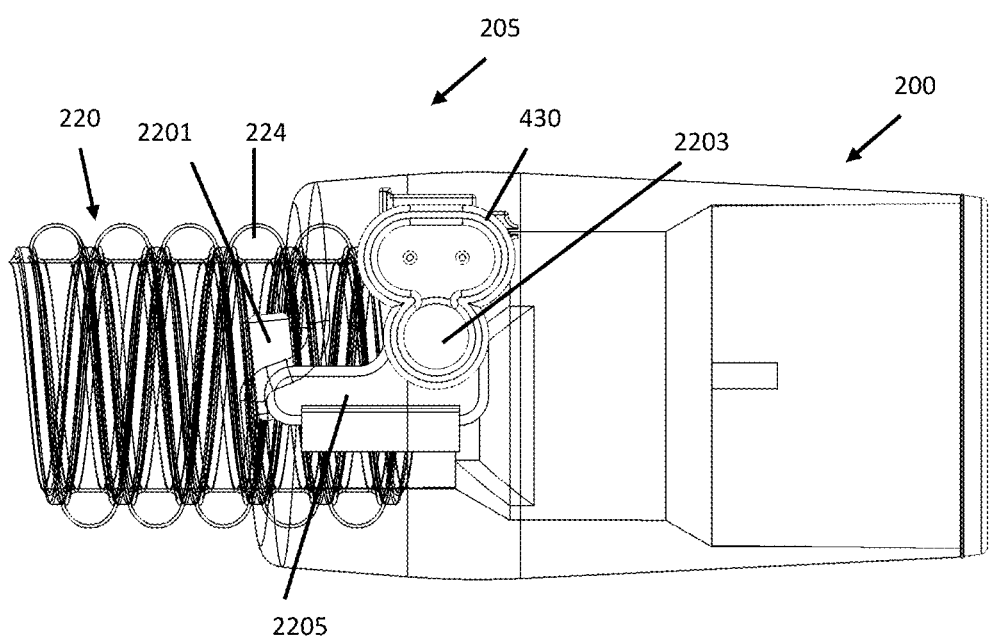
FIG. 22G shows a cross-sectional, bottom plan view of the medical circuit according to the embodiment of FIG. 22F.

FIGS. 22F and 22G show the inner conduit 2201 inserted into the first elongate member 224 of the medical tube 220. Gas flows from the lumen 830 of the first elongate member 224 and through the vent path 2205 and is exhausted through the membrane 2203 to the atmosphere. Desirably the power adaptor port 430 is close to the tube end of the connector 200 to decrease the length of the gases pathway 940. Such a configuration can simplify the manufacturing process, as the parts forming the gases pathway 940 are small and susceptible to breakage and a shorter pathway is less likely to be broken during manufacturing. FIGS. 22f and 22g do not show the probe port 425 to simplify illustration. It should be recognized that the power adaptor port 430 of FIGS. 22f and 22g can be used with the probe port 425 as described herein. In some embodiments, these parts are distinct and joined by overmolding. In some embodiments, the probe port 425 and the power adaptor port 430 can be a single part.

In some embodiments, the power adaptor port 430 may comprise a clamp (not shown) to aid with the manufacturing of the connector 200. The clamp may attach to the medical tube 220, for example to the second elongate member 228, such that it is held in place in relation to the power adaptor port 430 during manufacturing, in preparation for the application of the overmold 240. In some embodiments, the clamp may attach to the first elongate member 224.

As discussed in greater detail above, gaseous communication between the first elongate member 224 and the atmosphere can be provided—in other words, the first elongate member 224 can be vented to the atmosphere—through the unused lobe of the power adaptor port 430. As shown in FIGS. 22F and 22G, a portion of the medical tube 220 can extend into the connector 200 past the point where the inner conduit 2201 is inserted in the first elongate member 224. In some embodiments, a portion of the first elongate member 224 within the connector 200 is not vented. Some embodiments include the realization that, during autoclaving, the unvented portion of the first elongate member 224 is susceptible to collapsing or bursting. Some embodiments further include the realization that such collapsing or bursting of the first elongate member 224 can cause the internal surface of the connector 200 to become covered with plastic. This plastic can become degraded and/or can act as a dirt trap. Therefore, the first elongate member 224 in the connector 200 past the point where the inner conduit 2201 is inserted can be compressed or flattened during manufacture. It was realized that such compression or flattening can advantageously prevent the first elongate member 224 from collapsing or bursting during autoclaving.

Figure 23:
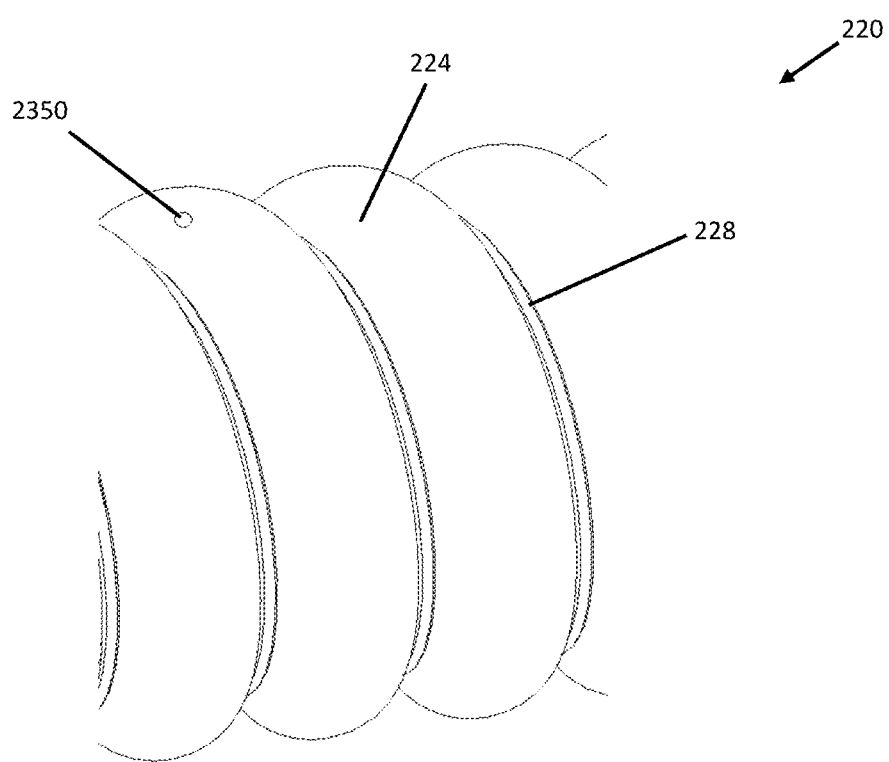
FIG. 23 shows a perspective view of a medical circuit according to an embodiment of the present disclosure.

FIG. 23 shows an embodiment wherein the lumen 830 (obscured) of the first elongate member 224 is open to the atmosphere. This establishes a gases flow path between the lumen 830 and the atmosphere. Thus, the medical tube 220 can be autoclaved without the use of the vent 720 or the vent 1520. In an embodiment, a cap (not shown) can close the opening in the first elongate 224. This enables the medical tube 220 to be soaked, by reducing or eliminating liquid and/or substance ingress into the first elongate member 224.

In the illustrated embodiment, the opening of the first elongate member 224 comprises a hole 2350. The hole 2350 may be positioned at any point along the first elongate member 224, for example, at one end of the first elongate member 224. The hole 2350 may comprise a small diameter such that it has a low surface tension. As a result, liquid and/or substances are less likely to flow through the hole 2350, but gases can flow to the atmosphere. In some embodiments the shape of the hole 2350 may differ, without departing from the scope of the present disclosure, for example, the hole 2350 may be shaped as a slit.

Figure 24A:
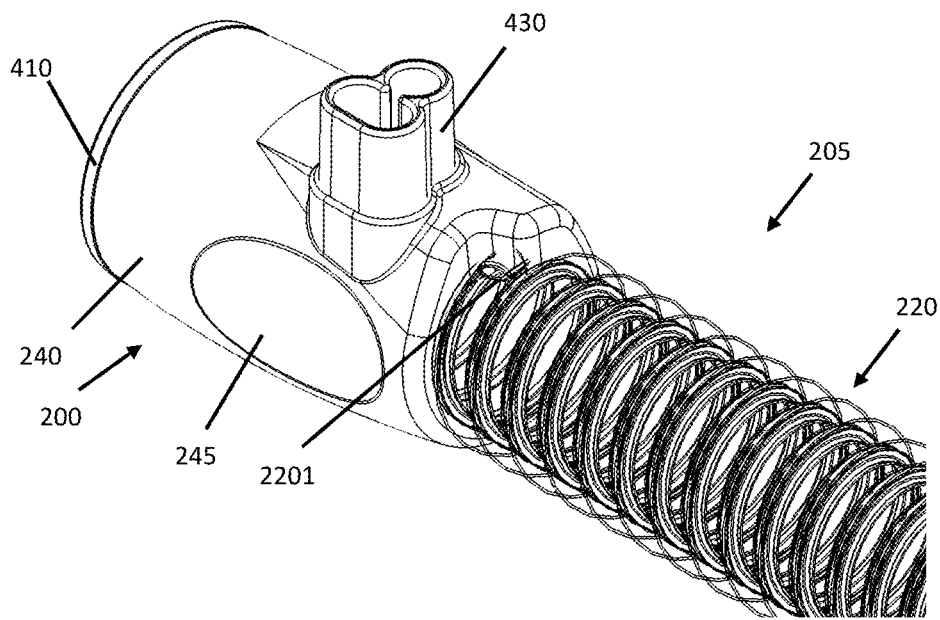
FIG. 24A shows an isometric view of a medical circuit according to an embodiment of the present disclosure.
Figure 24B:
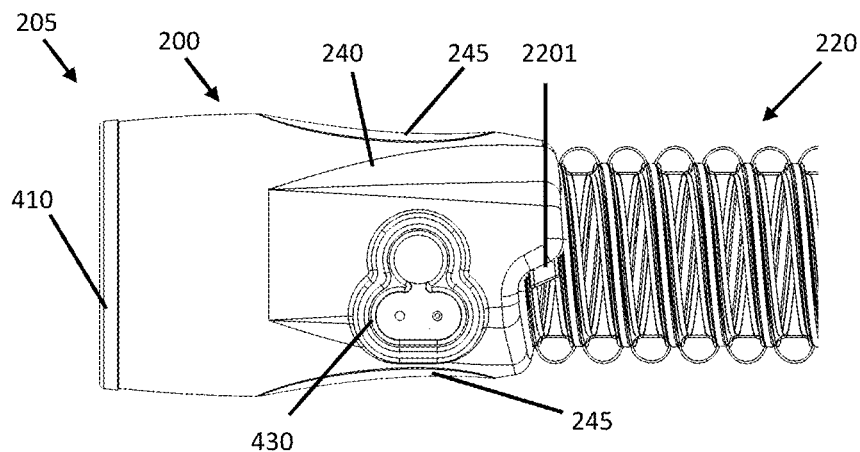
FIG. 24B shows a top plan view of the medical circuit according to the embodiment of FIG. 24A.
Figure 24C:
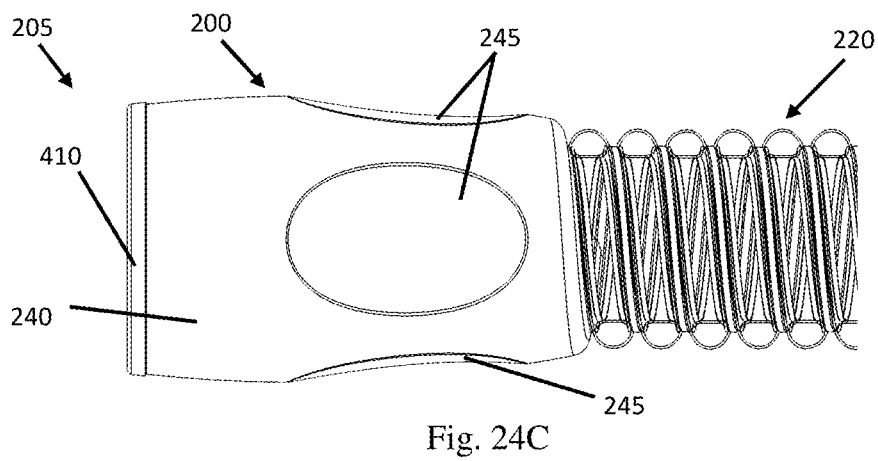
FIG. 24C shows a bottom plan view of the medical circuit according to the embodiment of FIG. 24A.

Generalized FIG. 24 shows the medical circuit 205 according to an embodiment of the present disclosure. FIG. 24A shows an isometric view of the medical circuit 205. FIG. 24B shows a top plan view of the medical circuit 205. FIG. 24C shows a bottom plan view of the medical circuit 205. The medical circuit 205 comprises the connector 200 and the medical tube 220. The features of the medical circuit 205 of generalized FIG. 24 are similar to those of the medical circuit 205 of generalized FIGS. 19, 20, and 21, and the discussions of generalized FIGS. 19, 20, and 21 are incorporated by reference. The embodiment of generalized FIG. 24 includes the power adaptor 430 but not the probe port 425. The embodiment of generalized FIG. 24 also includes the inner conduit 2201 of generalized FIG. 22. In FIGS. 24A and 24B, the medical tube 220 is depicted as transparent so that the inner conduit 2201 is visible.

Modifications described elsewhere in this disclosure can be incorporated in the embodiments of generalized FIG. 24.

Figure 25A:
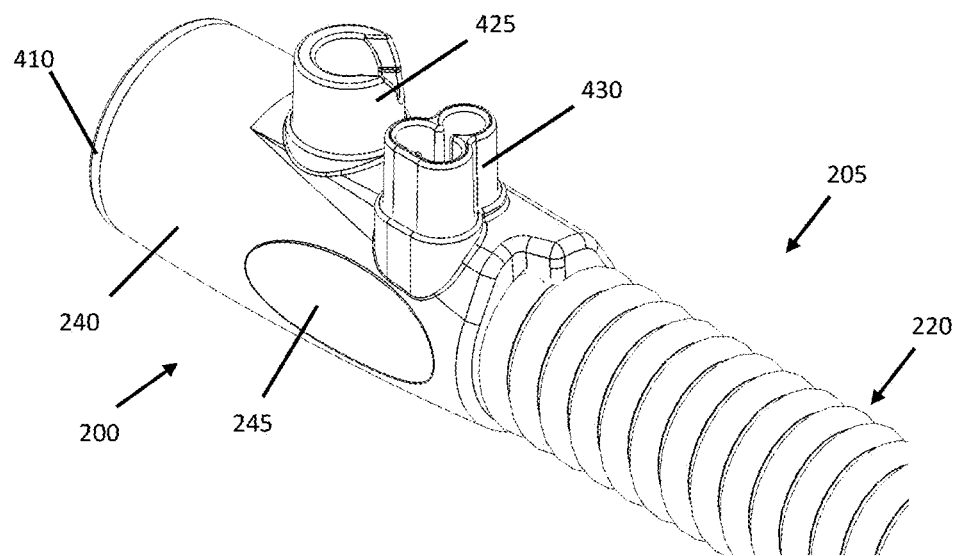
FIG. 25A shows an isometric view of a medical circuit according to an embodiment of the present disclosure.
Figure 25B:
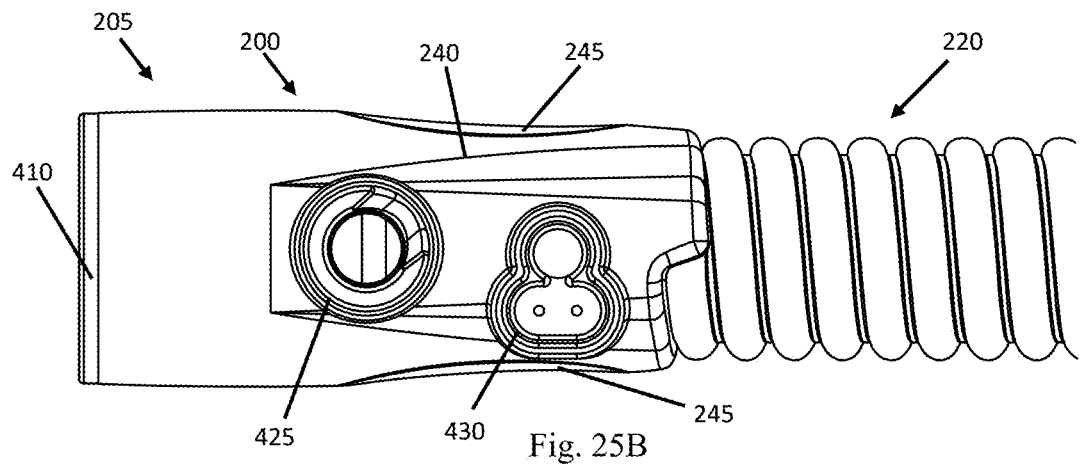
FIG. 25B shows a top plan view of the medical circuit according to the embodiment of FIG. 25A.
Figure 25C:
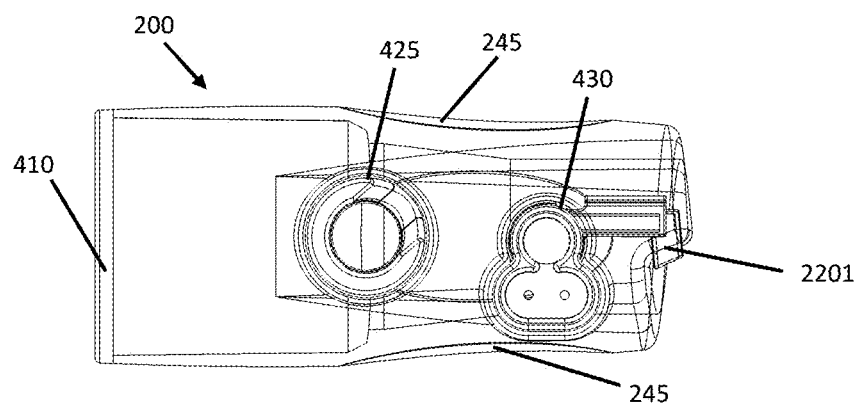
FIG. 25C shows a bottom plan view of a connector according to the embodiment of FIG. 25A.

Generalized FIG. 25 shows the medical circuit 205 according to an embodiment of the present disclosure. FIG. 25A shows an isometric view of the medical circuit 205. FIG. 25B shows a top plan view of the medical circuit 205. The medical circuit 205 comprises the connector 200 and the medical tube 220. FIG. 25C shows a bottom plan view of the connector 200. The features of the medical circuit 205 of generalized FIG. 25 are similar to those of the medical circuit 205 of generalized FIGS. 19, 20, 21, and 24, and the discussions of generalized FIGS. 19, 20, 21, and 24 are incorporated by reference. The embodiment of generalized FIG. 25 includes the power adaptor 430 and the probe port 425. The embodiment of generalized FIG. 25 also includes the inner conduit 2201 of generalized FIG. 22. In FIG. 25C, the connector 200 is shown without the medical tube 220 so that the inner conduit 2201 is visible.

Modifications described elsewhere in this disclosure can be incorporated in the embodiments of generalized FIG. 25.

The vent 720 and the vent 1520 may comprise a material that is chosen for its high heat temperature limits combined with manufacturability. An example of such a material is polytetrafluoroethylene (PTFE). The material may be permeable to gases but impermeable to liquids. For example, the material may have a low surface tension that does not allow liquids and/or substances to pass through the pores of the material. The medical tube 220 could be made from any material that is able to withstand autoclaving, high level disinfection, pasteurization, sterilisation or soaking in chemicals. Properties such as flexibility and weight of the medical tube 220 should be considered with material options.

In some embodiments, the vent 720 and the vent 1520 as discussed may comprise different shapes, sizes, or compositions. The length, depth, and diameter of the vent 720, or the thickness of the vent 1520, may be altered for specific applications. In an embodiment, the length, depth, and diameter of the vent 720, or the thickness of the vent 1520, can be chosen to maintain sufficient gases flow through the vent 720 and the vent 1520 while limiting liquid and/or substance ingress.

The length with relation to the cross-sectional area of the vent 720, or the thickness with relation to the cross-sectional area of the vent 1520, may have an effect on the liquid and/or substance ingress into the first elongate member 224. For purposes of example only, an increased length or decreased cross-sectional area of the vent 720 may further reduce liquid and/or substance ingress. Similarly, an increased thickness or decreased cross-sectional area of the vent 1520 may reduce liquid and/or substance ingress. A shorter length or increased cross-sectional area of the vent 720 may improve gases flow through the first elongate member 224. A thinner or increased cross-sectional area of the vent 1520 may improve gases flow through the first elongate member 224. Both the length or thickness, and the cross-sectional area, can be altered to optimise the vent 720, 1520 for the application. An optimised ratio between length or thickness, and cross-sectional area allows gases flow while reducing liquid and/or substance ingress through the vent 720, 1520.

The vent 720, 1520 allows a gases flow between the first elongate member 224 and the atmosphere. The vent 720, 1520, or the housing 1060, 1360, 1460, 1560, may be positioned at any point along the first elongate member 224 of the medical tube 220. In some embodiments, the vent 720, 1520 may be located at one end of the medical tube 220. In some embodiments, the vent 720, 1520 may be located at each end of the medical tube 220. In some embodiments, multiple of the vent 720, 1520 may be used.

In some embodiments, each of the housings 1060, 1360, 1460, 1560 may not comprise the vent 720, 1520. Thus, each of the housings 1060, 1360, 1460, 1560 may be empty. Each of the housings 1060, 1360, 1460, 1560 can be used to form the gases pathway 940 between the first elongate member 224 and the atmosphere. Each of the housings 1060, 1360, 1460, 1560 may comprise an opening or hole to pneumatically connect the first elongate member 224 to the atmosphere. As a result, the gases pathway 940 may comprise a hole or slit. A cap may be used to prevent liquid and/or substance ingress.

Maintaining gaseous communication between the first elongate member 224 and the atmosphere is important for reusable applications, as the medical tube 220 may be required to undergo rigorous cleaning routines such as autoclaving, pasteurizing and/or soaking in a substance. Autoclaving subjects the medical tube 220 to large pressure changes and high temperatures; by way of example only, the temperature during autoclaving could reach 134° C. The materials of the medical tube 220 can be chosen to withstand high temperatures. Gaseous communication between the vent 720, 1520 and the atmosphere allows gases to flow into/out of the first elongate member 224 as the pressure changes. This may prevent the first elongate member 224 from collapsing or bursting during autoclaving.

In some cases the circuit 205 may be required to withstand soakage for a period of time in a liquid or substance. The vent 720, 1520 can be used to prevent liquid and/or substance ingress into the first elongate member 224. The vent 720, 1520 enables the circuit 205 to withstand soakage for a typical period of time. The time may be in the range of 10 to 30 minutes, or in some cases may be anywhere in the range of 10 to 24 hours. The vent 720, 1520 enables the circuit 205 to be able to withstand different cleaning approaches such that the circuit 205 may be reused. The circuit 205 may be reusable for up to, but not limited to, 50 cycles. In an embodiment, the circuit 205 may be reused for greater than 50 cycles.

In an embodiment, the plurality of heater wires 1015 may be located within the second elongate member 228, such that they are integral to the medical tube 220. As a result, the plurality of heater wires 1015 are not exposed during cleaning. For example, the plurality of heater wires 1015 are not exposed to the liquid and/or substance during soakage of the circuit 205. Thus, the plurality of heater wires 1015 do not need to be removed prior to cleaning, and as such, the user is not required to perform any additional functions to prepare the circuit 205 for cleaning or for use on a patient.

It is to be understood that use of the medical tube 220 without the plurality of heater wires 1015, or with multiple of the plurality of heater wires 1015 is within the scope of the present disclosure. The second elongate member 228 may comprise a plurality of sensor wires. In some embodiments, the medical tube 220 may comprise any combination of the plurality of heater wires 1015 and the plurality of sensing wires.

In an embodiment, the vent 720, 1520 can be made from any material that is permeable to gases but impermeable to liquids.

In an alternative embodiment, the vent 720, 1520 can be made from stainless steel or brass. A stainless steel or brass embodiment of the vent 720, 1520 provides a pathway for the gases to flow during autoclaving, however it may not prevent liquid and/or substances from entering the first elongate member 224 during soaking of the circuit 205.

Additional Terminology

Unless the context clearly requires otherwise, throughout the description and the claims, the words "comprise," "comprising," and the like, are to be construed in an inclusive sense as opposed to an exclusive or exhaustive sense, that is to say, in the sense of "including, but not limited to."

Reference to any prior art in this specification is not, and should not be taken as, an acknowledgement or any form of suggestion that that prior art forms part of the common general knowledge in the field of endeavor in any country in the world.

The apparatus and system of the present disclosure may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the systems and apparatus described herein will be apparent to those skilled in the art. Such changes and modifications may be made without departing from the spirit and scope of the apparatus and systems of the present disclosure and without diminishing its attendant advantages. For instance, various components may be repositioned as desired. It is therefore intended that such changes and modifications be included within the scope of the present disclosure. Moreover, not all of the features, aspects and advantages are necessarily required to practice the apparatus and systems of the present disclosure. Accordingly, the scope of the present disclosure is intended to be defined only by the claims that follow.

What is claimed is:

1. A medical circuit for a gases delivery system, the medical circuit comprising:
   a medical tube, wherein the medical tube comprises a first elongate member and a second elongate member; and
   a connector having a first end, and external and internal surfaces extending from the first end to the tube end, the connector being configured to connect the medical tube to a gases delivery system component, the connector comprising:
   a plurality of rigid components,
   the tube end forming a connection with the medical tube, and
   an overmold at least partially surrounding the rigid components and comprising an offset portion formed by an exterior edge at the tube end delimiting the connector in the axial direction, wherein the offset portion is configured to allow a portion of the exterior edge delimiting the tube end of the connector to follow a helical orientation of the first elongate member.

2. The medical circuit of claim 1, the first elongate member comprising a lumen.

3. The medical circuit of claim 1, wherein the plurality of rigid components comprises at least a power adaptor port, the power adaptor port comprising an inner conduit inserted into the first elongate member.

4. The medical circuit of claim 1, wherein the second elongate member of the medical tube is configured to provide reinforcement to the medical tube.

5. The medical circuit of claim 1, wherein the medical tube further comprises heater wires embedded within the second elongate member.

6. The medical circuit of claim 1, the offset portion comprising a step within the exterior edge.

7. A connector for connecting to a medical gases delivery system component, the connector comprising:
   a first end;
   a tube end opposite the first end, the tube end configured to form a connection with a medical tube;
   a plurality of rigid components; and
   an overmold at least partially surrounding the plurality of rigid components, the overmold comprising an exterior edge at the tube end that delimits the connector in an axial direction, and the exterior edge delimiting the connector comprises an offset portion at the tube end, the offset portion of the exterior edge delimiting the connector configured to allow a portion of the exterior edge delimiting the tube end of the connector to follow a helical orientation of the medical tube.

8. The connector of claim 7, the offset portion comprising a step within the exterior edge.

9. The connector of claim 7, wherein the medical tube comprises a first elongate member comprising an inner lumen, and the offset portion is configured to allow a portion of the exterior edge to follow a helical orientation of the first elongate member.

10. The connector of claim 7, the overmold comprising an undercut.

11. The connector of claim 7, the plurality of rigid components comprising at least a carrier part and a power adapter port, wherein
the carrier part comprises a probe port configured to receive a sensing probe, the overmold forming an undercut on an internal surface of the probe port,
the overmold forms an undercut on an internal surface of the power adaptor port, and
a first protrusion surrounds the probe port and a second protrusion surrounds the power adaptor port, the first protrusion and the second protrusion configured to prevent the overmold from extending onto the probe port and the power adaptor port.

12. The connector of claim 11, further comprising a connection end, opposite the tube end, configured to connect with the medical gases delivery system component, wherein at least part of the probe port and at least part of the power adaptor port are aligned along a linear axis extending longitudinally from the tube end of the connector to the connection end of the connector.

13. The connector of claim 11, wherein the probe port and the power adaptor port are transverse to each other on a circumference of the connector.

14. The connector of claim 7, the plurality of rigid components comprising at least a rigid cuff, wherein
the overmold is configured to extend over the rigid cuff, the overmold further comprising a soft lip extending past the plurality of rigid components, and
the rigid cuff comprises a taper that is not covered by the overmold region, and further wherein a taper material forming the taper is more rigid than an overmold material forming the overmold.

15. The connector of claim 7, wherein the connector is configured to withstand multiple cleaning cycles such that the connector is reusable with a medical gases delivery system component and a medical tube.

16. A gases delivery system comprising:
a nasal cannula;
a medical circuit comprising:
a medical tube, wherein the medical tube comprises a first elongate member and a second elongate member; and
a connector having a first end, a tube end forming a connection with the medical tube, and a body extending between the first end and the tube end in an axial direction, the body comprising external and internal surfaces extending from the first end to the tube end, the connector being configured to connect the medical tube to the nasal cannula, the connector comprising:
an overmold at least partially surrounding the body and comprising an offset portion formed by an exterior edge at the tube end delimiting the connector, wherein the offset portion of the exterior edge delimiting the tube end of the connector enables a remainder of the exterior edge delimiting the connector at the tube end to follow a helical orientation of the first elongate member.

17. The gases delivery system of claim 16, the first elongate member comprising a lumen and the second elongate member is configured to provide reinforcement to the medical tube.

18. The gases delivery system of claim 16, wherein the offset portion comprises a step within the exterior edge.

19. A nasal oxygen delivery system comprising:
a cannula;
a medical circuit comprising:
a medical tube, wherein the medical tube comprises a first elongate member and a second elongate member; and
a connector having a first end, a second end, and a body extending in an axial direction between the first end and the second end and having a lumen configured to allow oxygen to pass through from the medical tube to the cannula, the body comprising external and internal surfaces extending from the first end to the second end, wherein the connector is connected to the medical tube at the first end and is configured to connect with the cannula at the second end, the connector comprising:
at least one rigid component;
an overmold at least partially surrounding the body and a portion of the medical tube, the overmold having an offset portion formed by an exterior edge delimiting the first end, the offset portion configured to allow a portion of the exterior edge delimiting the first end to follow a helical path of the medical tube;
a lip forming an outlet on the second end and configured to interact with the cannula; and
at least one radially extending protrusion on the body;
wherein the first end of the connector has a larger external diameter than the second end; and
wherein the first end of the connector is generally cylindrical.

20. The nasal oxygen delivery system of claim 19, wherein the first elongate member and the second elongate member cooperate to reduce the condensate formation and to maintain the humidity of the gases as they are transported within the medical tube.

21. The nasal oxygen delivery system of claim 19, wherein the connector comprises polypropylene and/or a thermoplastic elastomer.

* * * * *

UNITED STATES PATENT AND TRADEMARK OFFICE
CERTIFICATE OF CORRECTION

| | | |
|---|---|---|
| PATENT NO. | : 11,090,457 B2 | Page 1 of 1 |
| APPLICATION NO. | : 15/324235 | |
| DATED | : August 17, 2021 | |
| INVENTOR(S) | : Paul Joseph Moody | |

It is certified that error appears in the above-identified patent and that said Letters Patent is hereby corrected as shown below:

In the Claims

In Column 22, Line 21, Claim 1, delete "end," and insert --end, a tube end,--.

In Column 22, Line 60, Claim 7, delete "and the" and insert --the--.

In Column 23, Line 37, Claim 14, delete "overmold region, and" and insert --overmold, and--.

Signed and Sealed this
Nineteenth Day of July, 2022

*Katherine Kelly Vidal*

Katherine Kelly Vidal
*Director of the United States Patent and Trademark Office*